(12) United States Patent
Matsumoto et al.

(10) Patent No.: US 11,331,039 B2
(45) Date of Patent: May 17, 2022

(54) SPINAL-COLUMN ARRANGEMENT ESTIMATION-APPARATUS, SPINAL-COLUMN ARRANGEMENT ESTIMATION METHOD, AND SPINAL-COLUMN ARRANGEMENT ESTIMATION PROGRAM

(71) Applicant: Keio University, Tokyo (JP)

(72) Inventors: Morio Matsumoto, Tokyo (JP); Kota Watanabe, Tokyo (JP); Yoshimitsu Aoki, Yokohama (JP); Ran Choi, Yokohama (JP)

(73) Assignee: Keio University, Tokyo (JP)

( * ) Notice: Subject to any disclaimer, the term of this patent is extended or adjusted under 35 U.S.C. 154(b) by 492 days.

(21) Appl. No.: 16/077,872

(22) PCT Filed: Feb. 15, 2017

(86) PCT No.: PCT/JP2017/005504
§ 371 (c)(1),
(2) Date: Aug. 14, 2018

(87) PCT Pub. No.: WO2017/141958
PCT Pub. Date: Aug. 24, 2017

(65) Prior Publication Data
US 2020/0069243 A1 Mar. 5, 2020

(30) Foreign Application Priority Data
Feb. 15, 2016 (JP) .............................. JP2016-025824

(51) Int. Cl.
*A61B 5/00* (2006.01)
*A61B 5/107* (2006.01)

(52) U.S. Cl.
CPC .......... *A61B 5/4561* (2013.01); *A61B 5/0073* (2013.01); *A61B 5/0077* (2013.01); *A61B 5/1071* (2013.01); *A61B 5/1075* (2013.01)

(58) Field of Classification Search
CPC ..... A61B 5/107; A61B 5/4561; A61B 5/4566; A61B 5/0073; A61B 5/0077; A61B 5/0064
See application file for complete search history.

(56) References Cited

U.S. PATENT DOCUMENTS

2005/0113663 A1  5/2005  Tamez-Pena et al.
2014/0303522 A1  10/2014  Akimoto et al.
(Continued)

FOREIGN PATENT DOCUMENTS

EP  0140681 A2  5/1985
JP  2011-250998 A  12/2011
(Continued)

OTHER PUBLICATIONS

Extended European Search Report dated Jun. 12, 2019, issued in corresponding European Patent Application No. 17753214.0.
(Continued)

*Primary Examiner* — Jason M Ip
(74) *Attorney, Agent, or Firm* — Morgan, Lewis & Bockius LLP

(57) ABSTRACT

An image acquisition unit configured to acquire an image representing a three-dimensional shape of a surface of a human body, a spinal-column arrangement estimation-unit configured to estimate spinal-column arrangement of the human body using accumulated data, and an angle calculation unit configured to calculate at least one of a Cobb angle and a rotation angle from the estimated spinal-column arrangement are included.

8 Claims, 19 Drawing Sheets

(56) References Cited

U.S. PATENT DOCUMENTS

2015/0287184 A1  10/2015  Parent et al.
2015/0313566 A1  11/2015  Diers et al.

FOREIGN PATENT DOCUMENTS

| JP | 2015-535451 A | 12/2015 |
|---|---|---|
| KR | 10-2013-0033737 A | 4/2013 |
| WO | 2013/081030 A1 | 6/2013 |

OTHER PUBLICATIONS

Karachalios, MD et al., "Ten-Year Follow-Up Evaluation of a School Screening Program for Scoliosis: Is the Forward-Bending Test an Accurate Diagnostic Criterion for the Screening of Scoliosis?", Spine, vol. 24, No. 22, pp. 2318-2324 (1999).

Willner, "Moire Topography—A Method for School Screening of Scoliosis", Archives of Orthopedic and Trauma Surgery, vol. 95, pp. 181-185 (1979).

Daruwalla et al., "Moire Topography in Scoliosis: its accuracy in detecting the site and size of the curve", The Journal of Bone and Joint Surgery, vol. 67, pp. 211-213, (1985).

Berryman et al., "A new system for measuring three-dimensional back shape in scoliosis", Eur Spine J, vol. 17, pp. 663-672 (2008).

Phan et al., "Computer algorithms and applications used to assist the evaluation and treatment of adolescent idiopathic scoliosis: a review of published articles 2000-2009", Eur Spine J, vol. 20, pp. 1058-1068 (2011).

Ramirez et al., "A Support Vector Machines Classifier to Assess the Severity of Idiopathic Scoliosis From Surface Topography", IEEE Transactions on Information Technology in BioMedicine, vol. 10, pp. 84-91 (2006).

Kim et al., "Automatic Scoliosis Detection Based on Local Centroids Evaluation on Moire Topographic Images of Human Backs", IEEE Transaction on Medical Imaging, vol. 20, No. 12, pp. 1314-1320, Dec. 2001.

Jeno et al., "A 5-year epidemiological study on the prevalence rate of idiopathic scoliosis in Tokyo: school screening of more than 250,000 children", Springer, J Orthop Sci, vol. 16, pp. 1-6 (2011).

Saito et al., "Multiple Object Extraction from Aerial Imagery with Convolutional Neural Networks", Journal of Imaging Science and Technology, 60(1), pp. 010402-1-010402-9 (2016).

International Search Report (with partial translation) dated May 16, 2017, issued in corresponding International Patent Application No. PCT/JP2017/005504.

International Preliminary Report on Patentability dated Aug. 21, 2018, for the corresponding International Patent Application No. PCT/JP2017/005504.

Office Action dated Mar. 6, 2020 in Korean Application No. 10-2018-7024830.

FIG. 16A
FIG. 16B
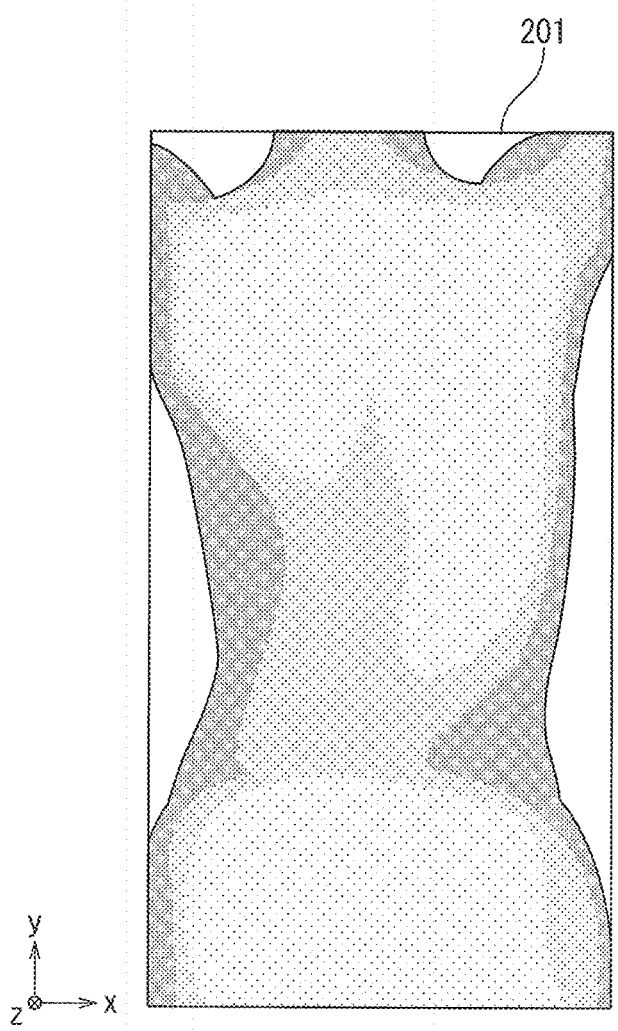
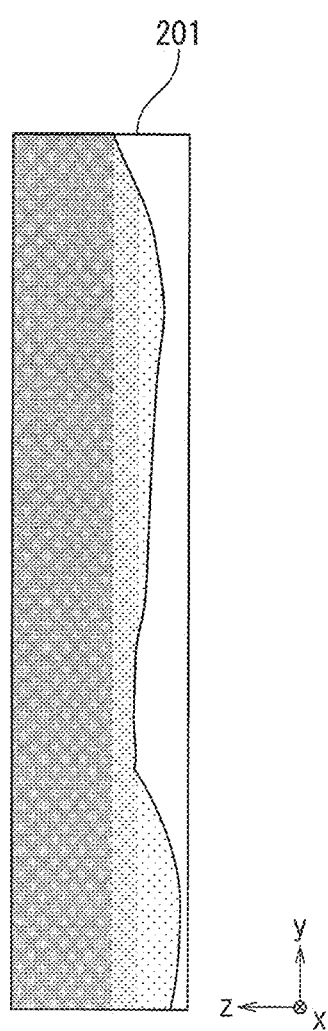

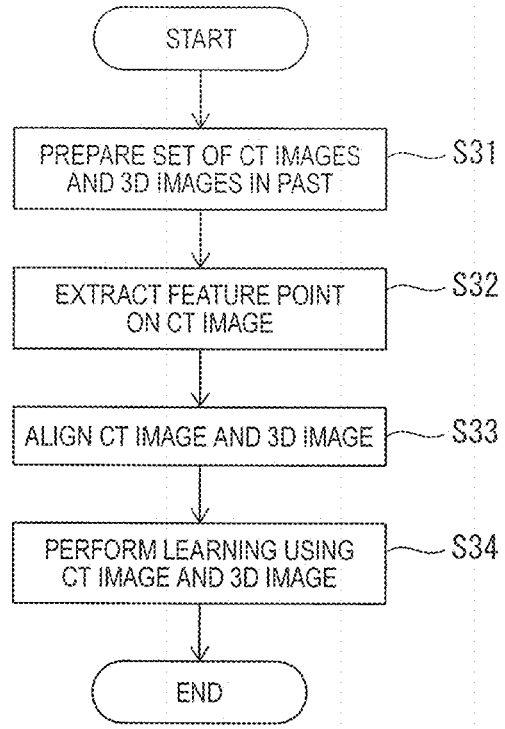

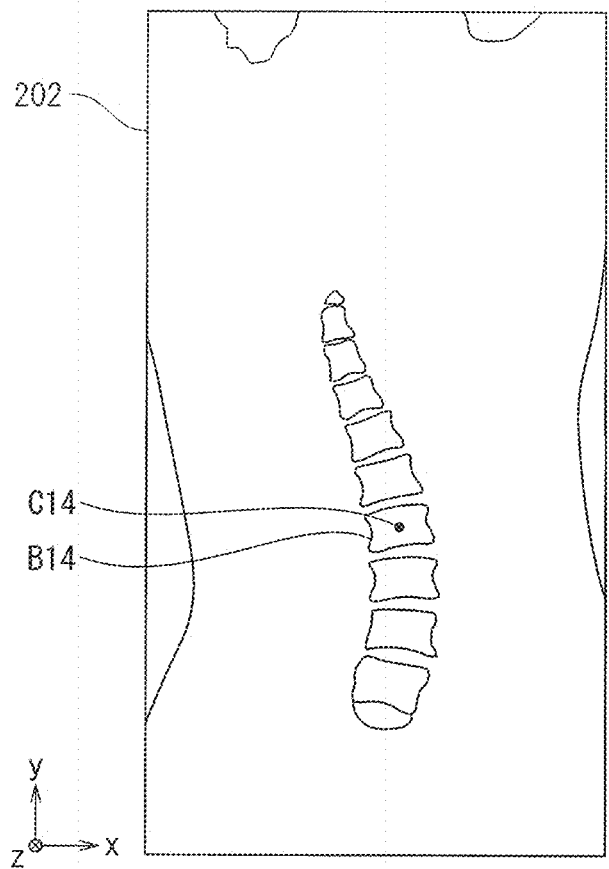
FIG. 18A
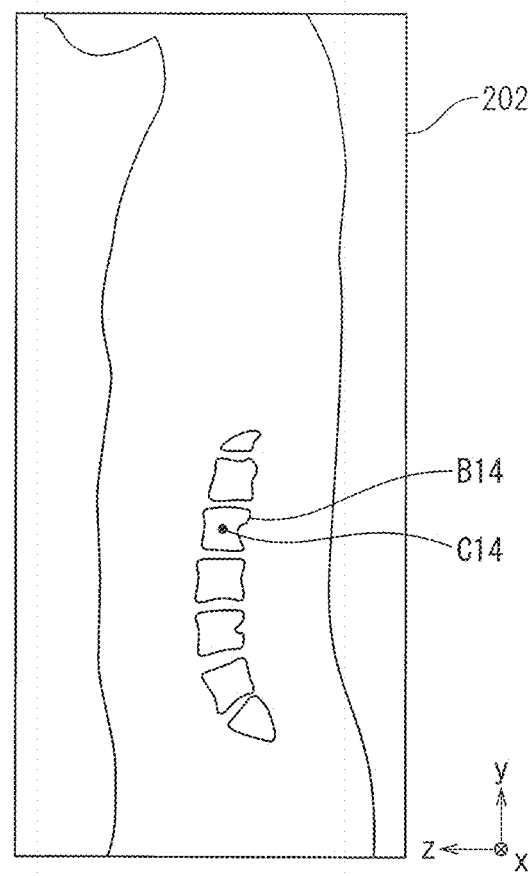
FIG. 18B
FIG. 18C
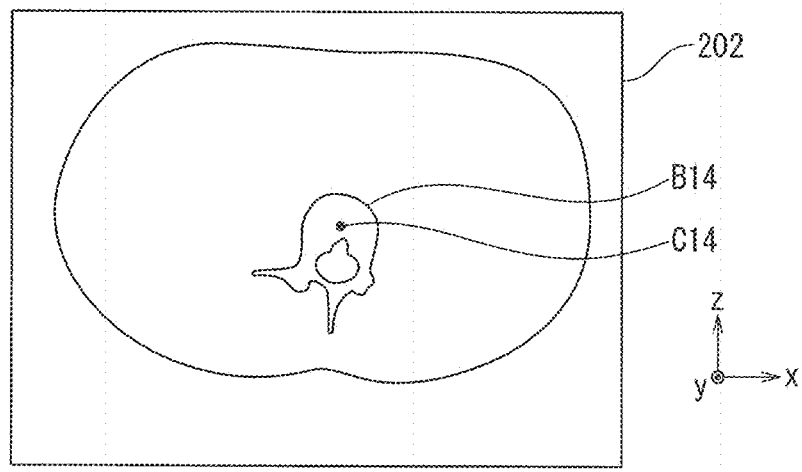

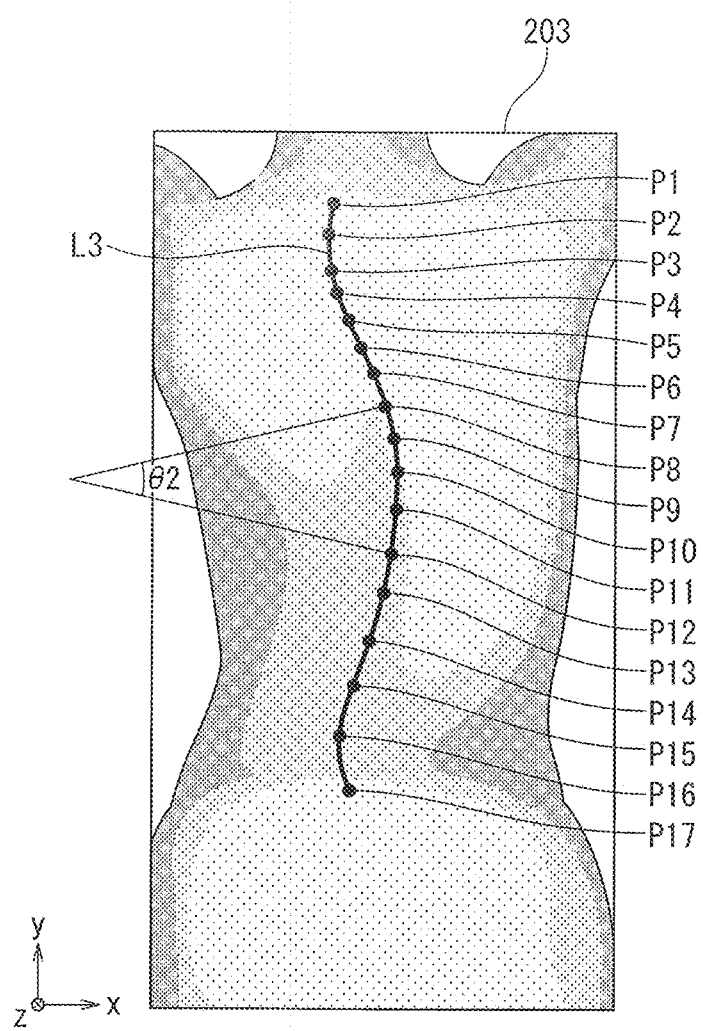 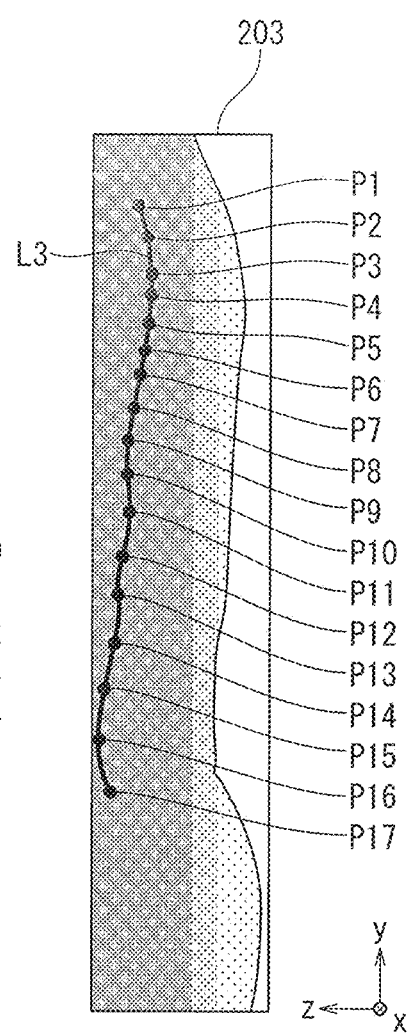

SPINAL-COLUMN ARRANGEMENT ESTIMATION-APPARATUS, SPINAL-COLUMN ARRANGEMENT ESTIMATION METHOD, AND SPINAL-COLUMN ARRANGEMENT ESTIMATION PROGRAM

TECHNICAL FIELD

The present invention relates to a spinal-column arrangement estimation-apparatus, a spinal-column arrangement estimation method, and a spinal-column arrangement estimation program.

BACKGROUND ART

Scoliosis is a disease in which a backbone (spine) normally linearly arranged when viewed from a front is laterally or longitudinally distorted. In Japan, according to the School Health and Safety Act, confirmation of a disease and abnormality of a spinal-column and thorax is obliged at the time of enrollment and regular checkup. A first checkup is carried out at each school at the instigation of a local government. When there is a doubt of scoliosis as a result of the first checkup, a second checkup is carried out, and X-ray photography test is performed to confirm the diagnosis of scoliosis.

In the first checkup, a lot of local governments use a moire test to determine the presence or absence of side curvature. As recited in Non-Patent Literatures (NPL) 1 and 2, in the moire test, an image of a back of a child is picked up using a moire fringe measuring device, a difference of elevation between right and left sides of the back is evaluated based on a difference in the number of moire fringes reflected in an obtained moire image, and the presence or absence of side curvature is determined.

However, there is no nationwide unified standard for determining the presence or absence of side curvature from the moire image, the moire test is independently implemented by each local government, and a variation arises in determination of the presence or absence of side curvature. For example, the sensitivity of the moire test is generally reported to be 100% and the specificity to be 86% (Karachalios, Spine 1999). However, in the second checkup conducted by the Tokyo Health Service Association in 2009, scoliosis of 32% of schoolchildren undergoing X-ray photography for the second checkup due to a doubt of scoliosis as a result of the first checkup has been denied, and it is desirable to reduce medical exposure by X-ray photography in such a case.

CITATION LIST

Non-Patent Literature

NPL 1: Willner S, "Moire' topography: a method for school screening of scoliosis", Archives of Orthopedic and Trauma Surgery (Arch Orthop Trauma Surg), (1979), Vol. 95: pp. 181-185.
NPL 2: Daruwalla J S, Balasubramanian P, "Moire' topography in scoliosis: its accuracy in detecting the site and size of the curve", The Journal of Bone and Joint Surgery (J Bone Joint Surg (Br)), (1985), Vol. 67, pp. 211-213.

SUMMARY OF INVENTION

Technical Problem

An object of the present invention is to provide a spinal-column arrangement estimation-apparatus, a spinal-column arrangement estimation method, and a spinal-column arrangement estimation program capable of estimating arrangement of spinal-column elements present inside a human body from an image representing a three-dimensional (3D) shape of a human body surface, facilitating diagnosis of scoliosis by a doctor, confirmation of a spinal-column by a determiner, etc., and reducing medical exposure by unnecessary X-ray inspection.

Solution to Problem

An aspect of the invention inheres in a spinal-column arrangement estimation-apparatus encompassing: (a) an image acquisition unit configured to acquire an image representing a 3D shape of a surface of a human body; (b) a spinal-column arrangement estimation-unit configured to estimate spinal-column arrangement from the acquired image using accumulated data; and (c) an angle calculation unit configured to calculate at least one of a Cobb angle and a rotation angle of the spinal-column arrangement based on the estimated spinal-column arrangement.

Another aspect of the invention inheres in a spinal-column arrangement estimation method encompassing: (a) a step of acquiring an image representing a 3D shape of a surface of a human body; (b) a step of estimating spinal-column arrangement from the acquired image using accumulated data; and (c) a step of calculating at least one of a Cobb angle and a rotation angle of the spinal-column arrangement based on the estimated spinal-column arrangement.

Further another aspect of the invention inheres in a spinal-column arrangement estimation program for causing a computer to execute: (a) an action configured to cause an image acquisition unit to acquire an image representing a 3D shape of a surface of a human body; (b) an action configured to cause a spinal-column arrangement estimation-unit to estimate spinal-column arrangement from the acquired image using accumulated data; and (c) an action configured to cause an angle calculation unit to calculate at least one of a Cobb angle and a rotation angle of the spinal-column arrangement based on the estimated spinal-column arrangement.

In the present invention, "accumulated data" refers to learning data machine-learned from clinical image data acquired in a clinical place. Examples of the clinical image data include X-ray image data, computed tomography (CT) image data, etc. However, the clinical image data is not limited to the X-ray image data or the CT image data. Examples of machine leaning include deep learning, etc. However, machine leaning is not limited to the deep learning.

Advantageous Effects of Invention

According to the present invention, it is possible to provide a spinal-column arrangement estimation-apparatus, a spinal-column arrangement estimation method, and a spinal-column arrangement estimation program capable of estimating arrangement of spinal-column elements present inside a human body from an image representing a 3D shape of a human body surface, facilitating diagnosis of scoliosis by a doctor, confirmation of a spinal-column by a determiner, etc., and reducing medical exposure by unnecessary X-ray inspection.

BRIEF DESCRIPTION OF DRAWINGS

FIG. 16A and FIG. 16B are schematic diagrams illustrating an example of a 3D image for machine learning according to a second embodiment of the present invention when viewed from different directions, respectively;

FIG. 17 is a flowchart for description of an example of a machine learning method according to the second embodiment of the present invention;

FIG. 18A to FIG. 18C are schematic diagrams illustrating an example of a CT image for machine learning according to the second embodiment of the present invention when viewed from different directions, respectively;

FIG. 20A and FIG. 20B are schematic diagrams illustrating an example of a 3D image including an estimation result of spinal-column arrangement according to the second embodiment of the present invention when viewed from different directions, respectively;

DESCRIPTION OF EMBODIMENTS

Figure 1:
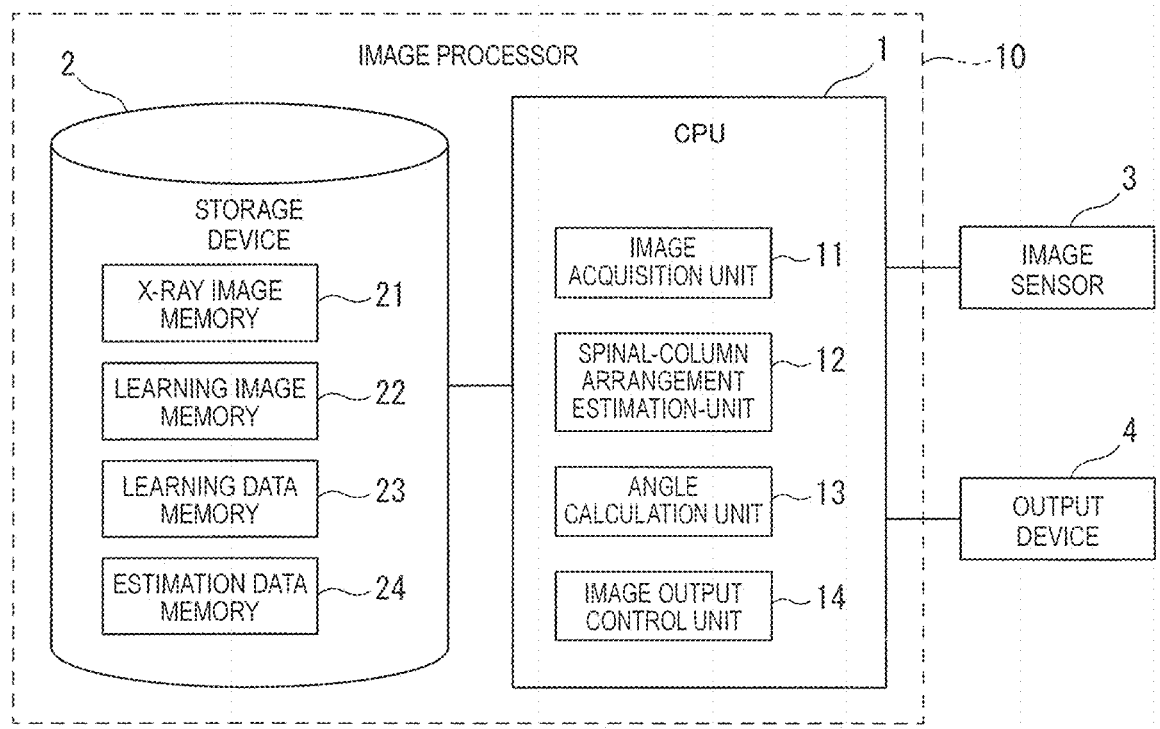
FIG. 1 is a schematic diagram illustrating an example of a spinal-column arrangement estimation-apparatus according to a first embodiment of the present invention.

With reference to the drawings, first and second embodiments of the present invention will be explained in detail below. In the following description of the drawings, the same or similar reference numerals are assigned to the same or similar portions. The drawings are schematic, and it should be noted that the relationship between thickness and planer dimensions, the thickness proportion of each layer, and the like are different from real ones. Accordingly, specific thicknesses or dimensions should be determined with reference to the following description. Moreover, in some drawings, portions are illustrated with different dimensional relationships and proportions.

The first and second embodiments described below merely illustrate schematically devices and methods for specifying and giving shapes to the technical idea of the present invention, and the span of the technical idea is not limited to materials, shapes, structures, and relative positions of elements described herein. The technical idea of the present invention is to cover various modifications falling within the scope of the invention as defined by the following appended claims.

First Embodiment

<Spinal-Column Arrangement Estimation-Apparatus>

As illustrated in FIG. 1, a spinal-column arrangement estimation (SCAE) apparatus according to a first embodiment of the present invention includes an image processor 10, an image sensor 3, and an output device 4. The image processor 10 may be implemented by a computer having a central processing unit (CPU) 1 and a storage device 2, or alternatively, the image processor 10 may be implemented by a processor, a programmable logic device (PLD) such as an FPGA, an integrated circuit, etc., which are equivalent to the computer.

Figure 2:
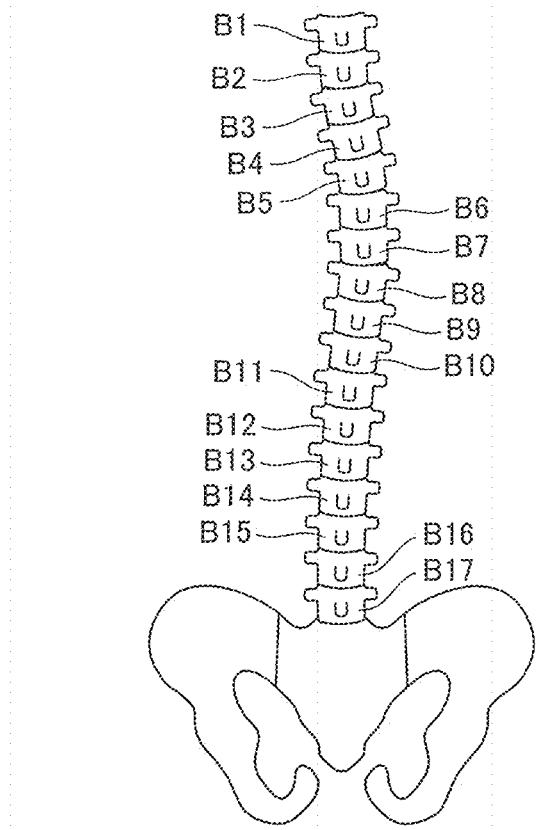
FIG. 2 is a schematic diagram illustrating an example of arrangement of spinal-column elements for description of scoliosis.

Arrangement of spinal-column elements estimated by the SCAE apparatus according to the first embodiment of the present invention is effective in determining the presence or absence of side curvature of a spinal-column and diagnosis of scoliosis. In general, a human spine (backbone) includes seven cervical vertebrae, twelve thoracic vertebrae, and five lumbar vertebrae as spinal-column elements in order from a head side. In the case of a healthy subject, the spinal-column is substantially straight with respect to a front or a back of a human. However, in the case of a scoliosis patient, as illustrated in FIG. 2, a symptom of laterally bending due to twisting is noticeable. FIG. 2 illustrates twelve thoracic vertebrae B1 to B12 and five lumbar vertebrae B13 to B17 in the spinal-column. Hereinafter, in this specification, the "cervical vertebrae", the "thoracic vertebrae" and the "lumbar vertebrae" corresponding to elements included in the spinal-column are collectively referred to as "spinal-column element". A definition of the spinal-column element as a generic name may further include "sacral vertebra" and "caudal vertebra" below the lumbar vertebrae.

Figure 3:
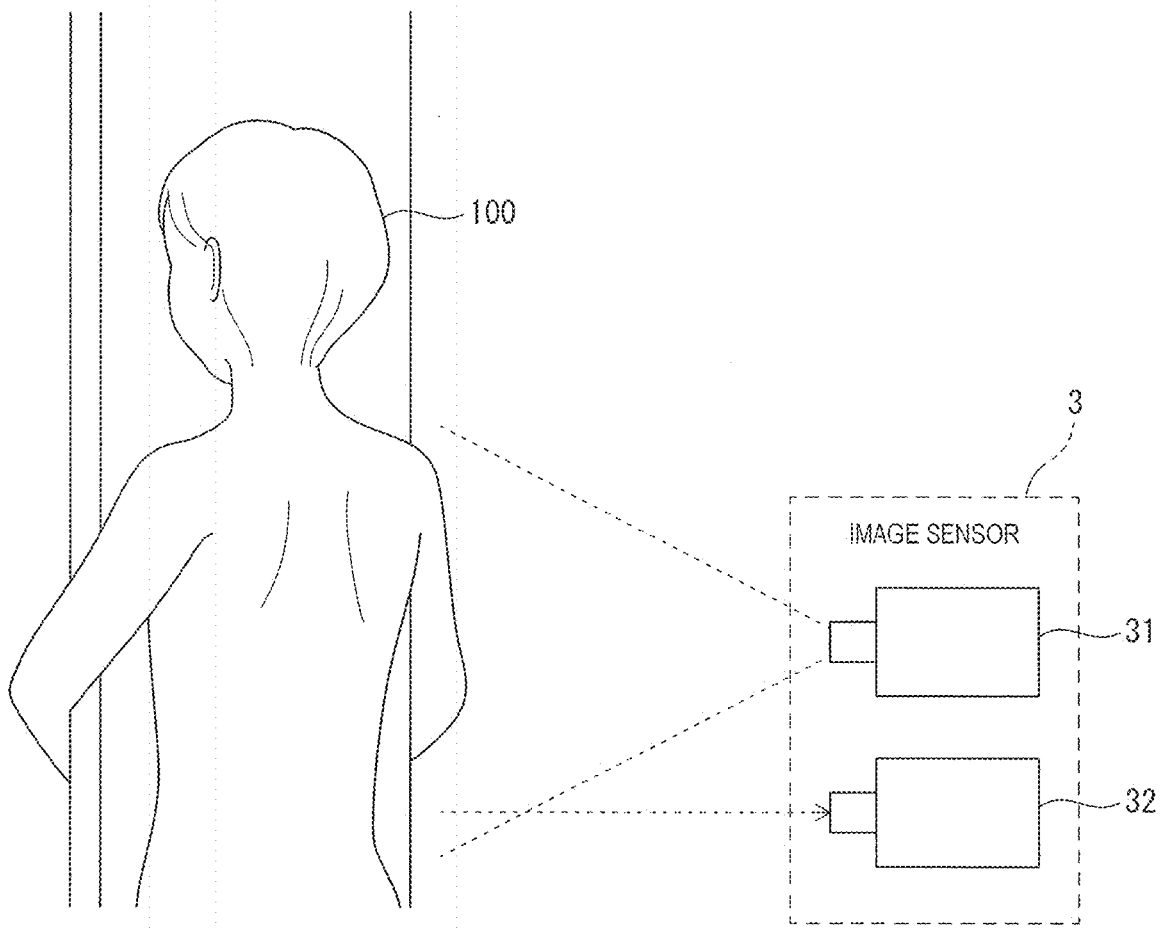
FIG. 3 is a schematic diagram illustrating an example of an image sensor according to the first embodiment of the present invention.

The image sensor 3 illustrated in FIG. 1 is a device capable of capturing an image representing a 3D shape of a human body surface. In the first embodiment, a description will be given of a case in which the image sensor 3 is a moire sensor (moire fringe measuring device) that captures a moire image including a moire fringe representing a 3D shape of a back of a human body. For example, as illustrated in FIG. 3, the moire sensor as the image sensor 3 includes a light projecting unit 31 that projects a pattern on the back of the human body 100 and a camera 32 that photographs the back of the human body 100. For example, a 3D scanner, a CCD camera, etc. may be used as the image sensor 3, and the image sensor 3 is not particularly limited as long as the device can capture a moire image or a two-dimensional (2D) image equivalent to the moire image.

Figure 4:
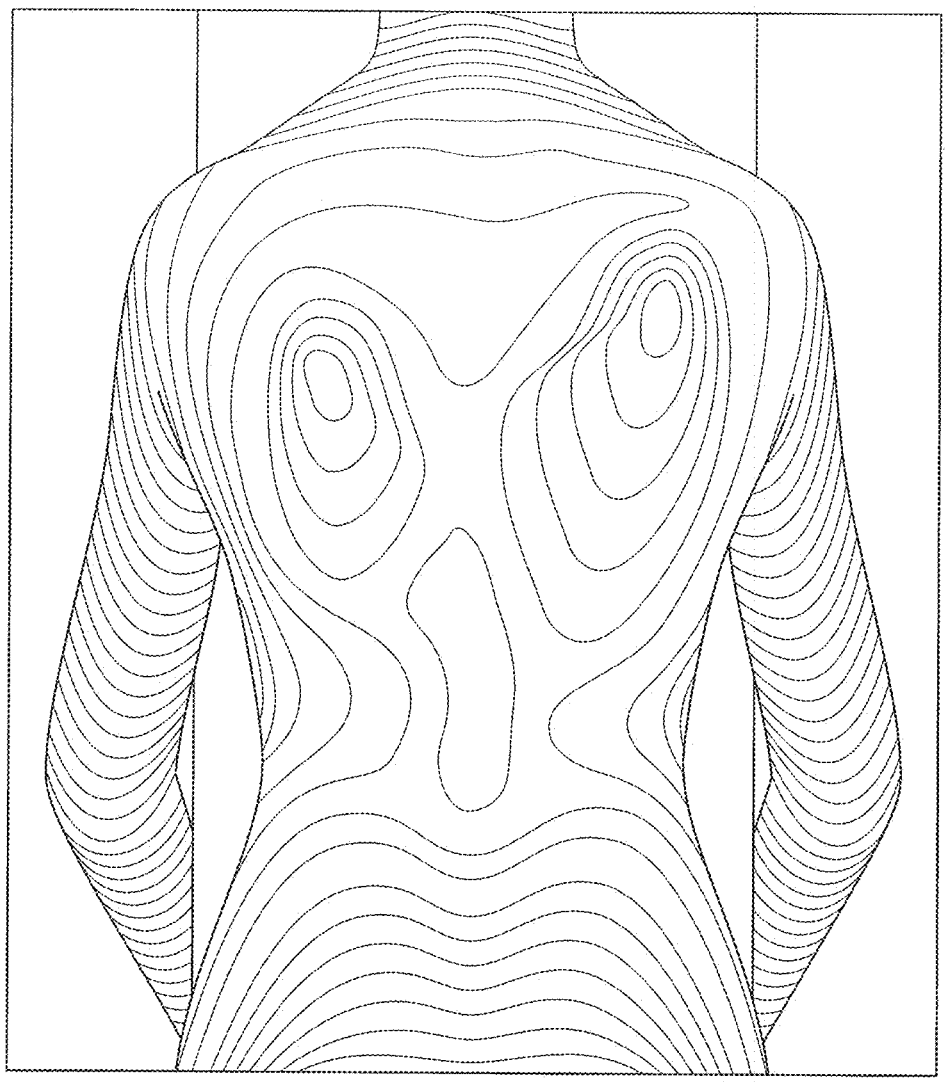
FIG. 4 is a schematic diagram illustrating an example of a moire image for machine learning according to the first embodiment of the present invention.

For example, the image sensor 3 captures a moire image 101 illustrated in FIG. 4. Moire fringes representing the 3D shape of the back of the human body are reflected in the moire image 101. In the case of the scoliosis patient, a difference of elevation of the back of the human body becomes large between the left and the right, and the number and shape of the moire fringes are different between the left and the right.

The CPU 1 includes an image acquisition unit 11, a spinal-column arrangement estimation (SCAE) unit 12, an angle calculation unit 13, and an image output control unit 14 as logic circuits, or logic modules, which can be conceived as hardware resources in computer system. Among these units, the SCAE unit 12 is the logic circuit, or the logic module in a system of artificial intelligence, which can execute machine learning such as deep learning. And therefore, the SCAE unit 12 performs a sequence of calculation processings so as to automatically and directly estimate spinal-column arrangement (spinal-column shape), from the moire image acquired by the image acquisition unit 11.

For example, a hardware resource that executes a computer software program such as a hierarchical neural network such as a convolution neural network (CNN) or a support vector machine (SVM) may be used as the artificial intelligence (AI), or hardware resources of a computer system, which implements the SCAE unit 12.

For example, a semiconductor memory, a magnetic disk, an optical disc, may be used as the storage device 2. As illustrated in FIG. 1, the storage device 2 includes an X-ray image memory 21 that stores a large number of past X-ray images for machine learning by the SCAE unit 12 a learning image memory 22 that stores a large number of past moire images for machine learning by the SCAE unit 12 a learning data memory 23 that stores learning data such as a weight parameter corrected by machine learning by the SCAE unit 12 and an estimation data memory 24 that stores estimation data such as an estimation result of a spinal-column element by the SCAE unit 12.

The storage device 2 may further include registers or a cache memory in the CPU 1, or a cache memory allocated adjacent to the CPU 1, other virtual storage devices, etc., which stores a spinal-column arrangement estimation (SCAE) program executed by the CPU 1, or alternatively, various data necessary for execution of the SCAE program. FIG. 1 schematically represents the storage device 2 as an image of hardware resources including registers and cache memories as a logical architecture, and may not represent a physical configuration, actually.

For example, a display such as a liquid crystal display (LCD) of a personal computer (PC) or a tablet terminal, a printer, a projector, a speaker, etc. may be used as the output device 4.

<Learning Phase>

Figure 5:
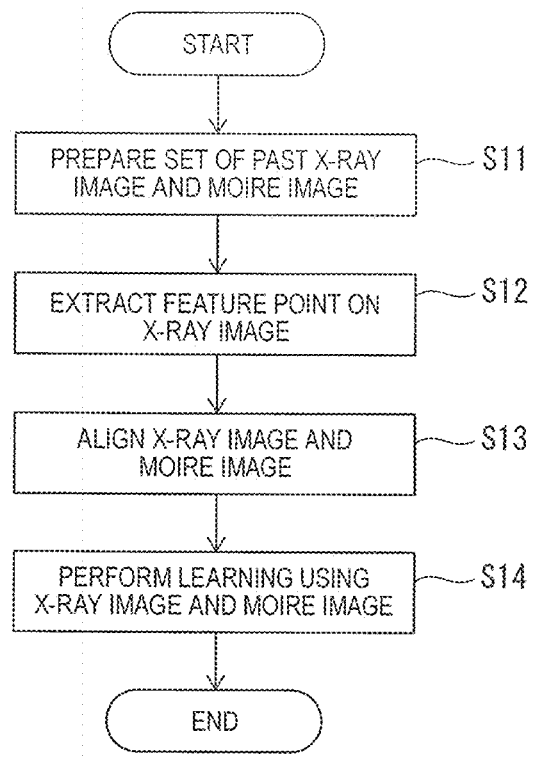
FIG. 5 is a flowchart for description of an example of a machine learning method according to the first embodiment of the present invention.

Here, a description will be given of an example of a "learning phase" including a machine learning method of the SCAE unit 12 according to the first embodiment with reference to a flowchart of FIG. 5. Here, a case in which the SCAE unit 12 includes the CNN will be illustrated.

In step S11, a large number of data sets (for example, thousands of sets) of moire images and X-ray images captured for the same person in the past are prepared as advance preparation for machine learning by the SCAE unit 12. The moire images and X-ray images captured for the same person are practically preferable as a data set. However, the present invention is not limited to the same person. For example, it is possible to adopt the moire images and X-ray images captured for respective people having similar body types as a data set. Each of a large number of moire images and X-ray images is stored in the learning image memory 22 and the X-ray image memory 21 of the storage device 2.

Figure 6:
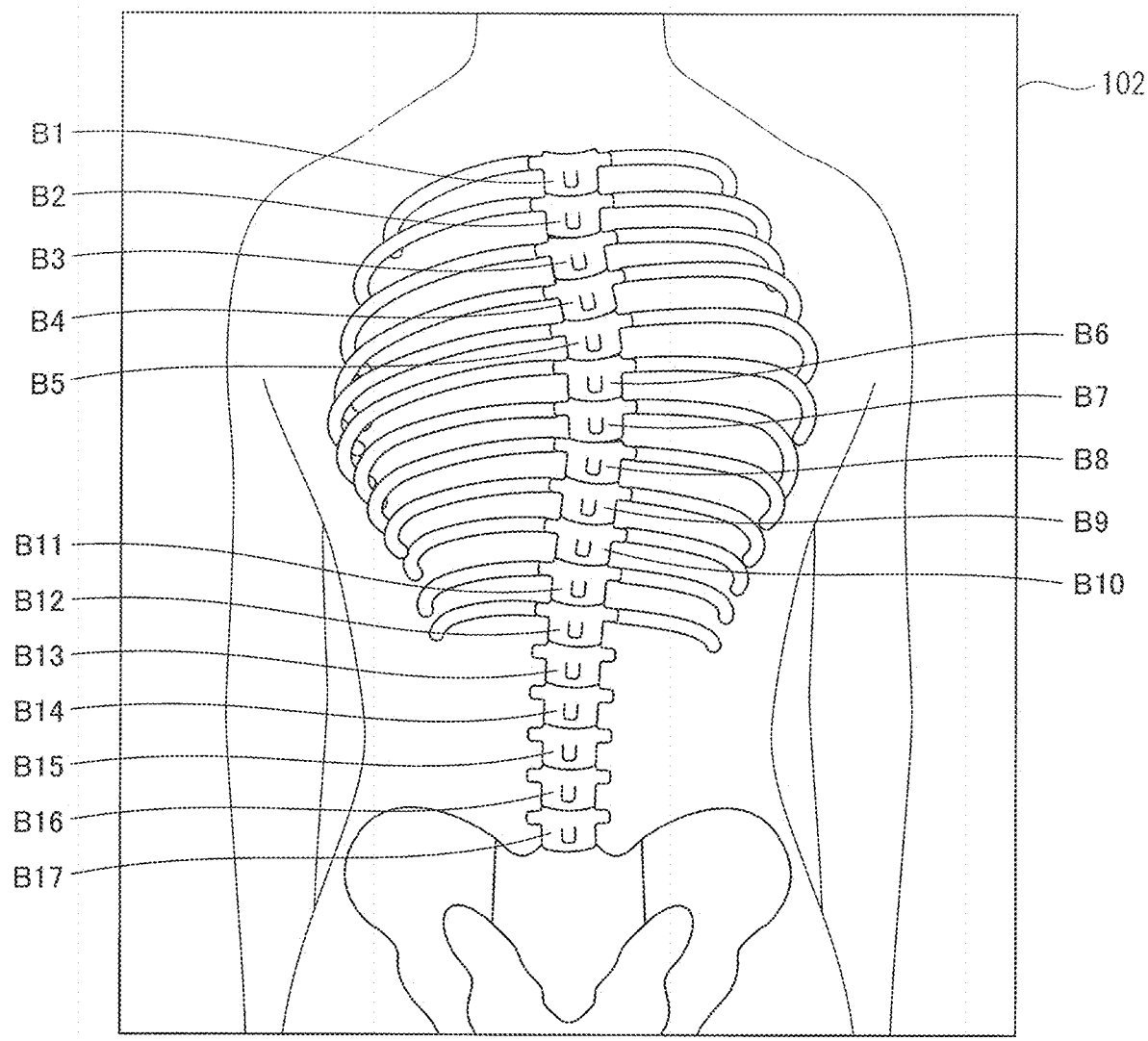
FIG. 6 is a schematic diagram illustrating an example of an X-ray image for machine learning according to the first embodiment of the present invention.

For example, a large number of sets of moire images 101, one (set) of which is illustrated in FIG. 4, are stored in the learning image memory 22, and a large number of sets of X-ray images 102, one (set) of which is illustrated in FIG. 6, are stored in the X-ray image memory 21. As illustrated in FIG. 6, one (one set of) X-ray image 102 is a standing X-ray front image viewed from a back side of a standing person. The twelve thoracic vertebrae B1 to B12 and the five lumbar vertebrae B13 to B17 among the spinal-column elements are reflected in the X-ray images 102.

Subsequently, in step S12 of FIG. 5, labeling of correct answer data used for machine learning is performed. The SCAE unit 12 extracts and reads one (one set of) X-ray image 102 from the X-ray image memory 21, and extracts an anatomical feature point (landmark) of the thoracic vertebrae B1 to B12 and the lumbar vertebrae B13 to B17 on the X-ray images 102.

Figure 7:
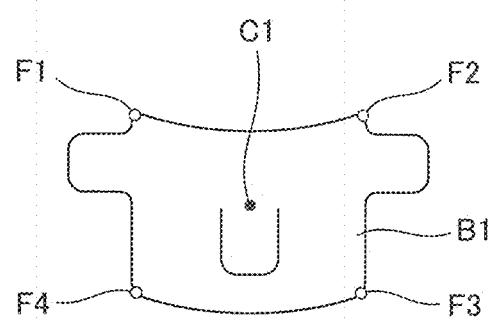
FIG. 7 is a schematic diagram illustrating an example of a spinal-column on the X-ray image according to the first embodiment of the present invention.

For example, the SCAE unit 12 performs edge extraction and binarization on the X-ray images 102. Further, as illustrated in FIG. 7, the SCAE unit 12 rectangle-approximates the thoracic vertebra B1 reflected in the X-ray images 102, extracts four points F1 to F4 corresponding to four corners of the rectangle-approximated thoracic vertebra B1 as anatomical feature points (landmarks), and calculates coordinates of the four points F1 to F4 on the X-ray images 102. The calculated coordinates of the four points F1 to F4 on the X-ray images 102 are stored in the learning data memory 23. Likewise, X-ray images are read from the X-ray image memory 21 for a large number of other sets, and coordinates as respective anatomical feature points (landmarks) are stored in the learning data memory 23.

Further, the SCAE unit 12 reads coordinates of four points F1 to F4 of a specific set on the X-ray images 102 from the learning data memory 23, extracts a centroid C1 of a rectangle-approximated thoracic vertebrae B1 as an anatomical feature point (landmark), and calculates coordinates $(X_{r1}, Y_{r1})$ of the centroid C1 on the X-ray images 102. The calculated coordinates $(X_{r1}, Y_{r1})$ of the centroid 1 on the X-ray images 102 are stored in the learning data memory 23.

In the first embodiment, the SCAE unit 12 rectangle-approximates the thoracic vertebra B1, and extracts the centroid C1 of the rectangle-approximated thoracic vertebra B1 as the anatomical feature point. However, the present invention is not limited to the centroid C1 as the anatomical feature point, and another anatomical feature point may be extracted.

Figure 8:
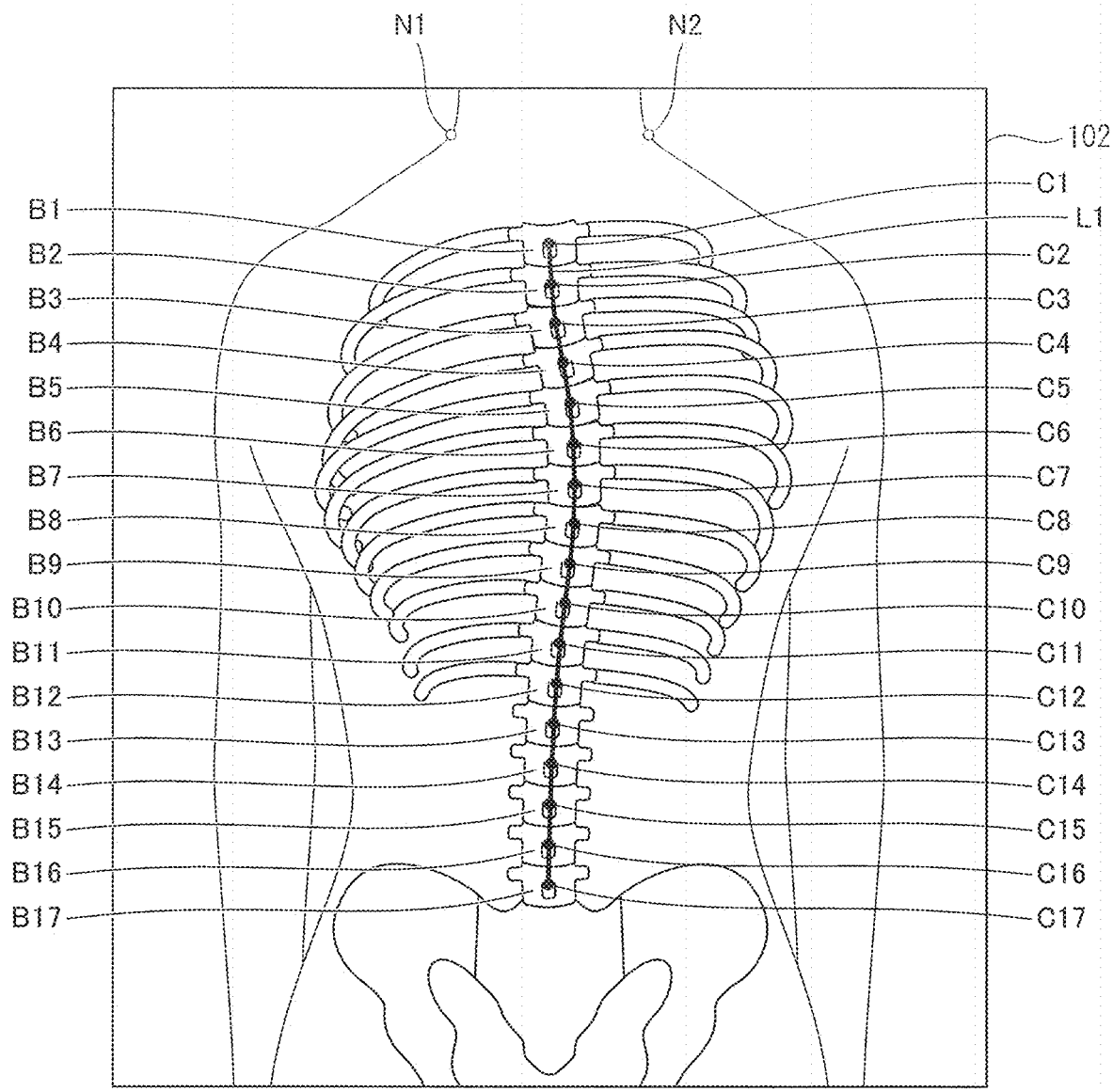
FIG. 8 is a schematic diagram illustrating an example of labeling of the X-ray image according to the first embodiment of the present invention.

As illustrated in FIG. 8, the SCAE unit 12 similarly extracts centroids C2 to C17 for the other thoracic vertebrae B2 to B12 and lumbar vertebrae B13 to B17, and calculates coordinates $(X_{ri}, Y_{ri})$ (i=2 to 17) of the centroids C2 to C17 on the X-ray images 102. The calculated coordinates $(X_{ri}, Y_{ri})$ (i=2 to 17) of the centroids C2 to C17 on the X-ray images 102 are stored in the learning data memory 23.

Further, as illustrated in FIG. 8, the SCAE unit 12 calculates a curve L1 for connecting the centroids C1 to C17 of the thoracic vertebrae B1 to B12 and the lumbar vertebrae B13 to B17 using the coordinates $(X_{ri}, Y_{ri})$ (i=1 to 17) of the centroids C1 to C17 of the thoracic vertebrae B1 to B12 and the lumbar vertebrae B13 to B17. For example, a B-spline curve, etc. may be adopted as the curve L1. The calculated curve L1 is stored in the learning data memory 23. The above-described processing in step S12 is performed for each of a large number of X-ray images stored in the X-ray image memory 21, and the curve L1 calculated for each set is stored in the learning data memory 23.

Subsequently, in step S13 of FIG. 5, the SCAE unit 12 reads, for example, the moire images and X-ray images for the same person corresponding to a data set from the learning image memory 22 and the X-ray image memory 21, respectively, and aligns the moire images and the X-ray images. When the moire images and the X-ray images for the same person are captured at the same time in the same posture, a step of alignment in step S12 is unnecessary. However, in general, the moire images and the X-ray images are captured at different timings, and misalignment occurs in posture in many cases.

Therefore, for example, as illustrated in FIG. 8, the SCAE unit 12 extracts two points N1 and N2 of a base of a neck of the human body reflected in the X-ray images 102 read from the X-ray image memory 21 as alignment marks, and stores coordinates of the two points N1 and N2 on the X-ray images 102 in the learning data memory 23. Further, as illustrated in FIG. 9, the SCAE unit 12 extracts two points N3 and N4 of the base of the neck of the human body as alignment marks for the moire images 101 read from the learning image memory 22, and stores coordinates of the two points N3 and N4 on the moire images 101 in the learning data memory 23.

Further, the SCAE unit 12 adjusts sizes of the moire images 101 and the X-ray images 102 and performs rotation, parallel translation, etc. so that the two points N1 and N2 of the base of the neck of the moire images 101 read from the learning data memory 23 coincide with the two points N3 and N4 of the base of the neck of the X-ray images 102.

Figure 9:
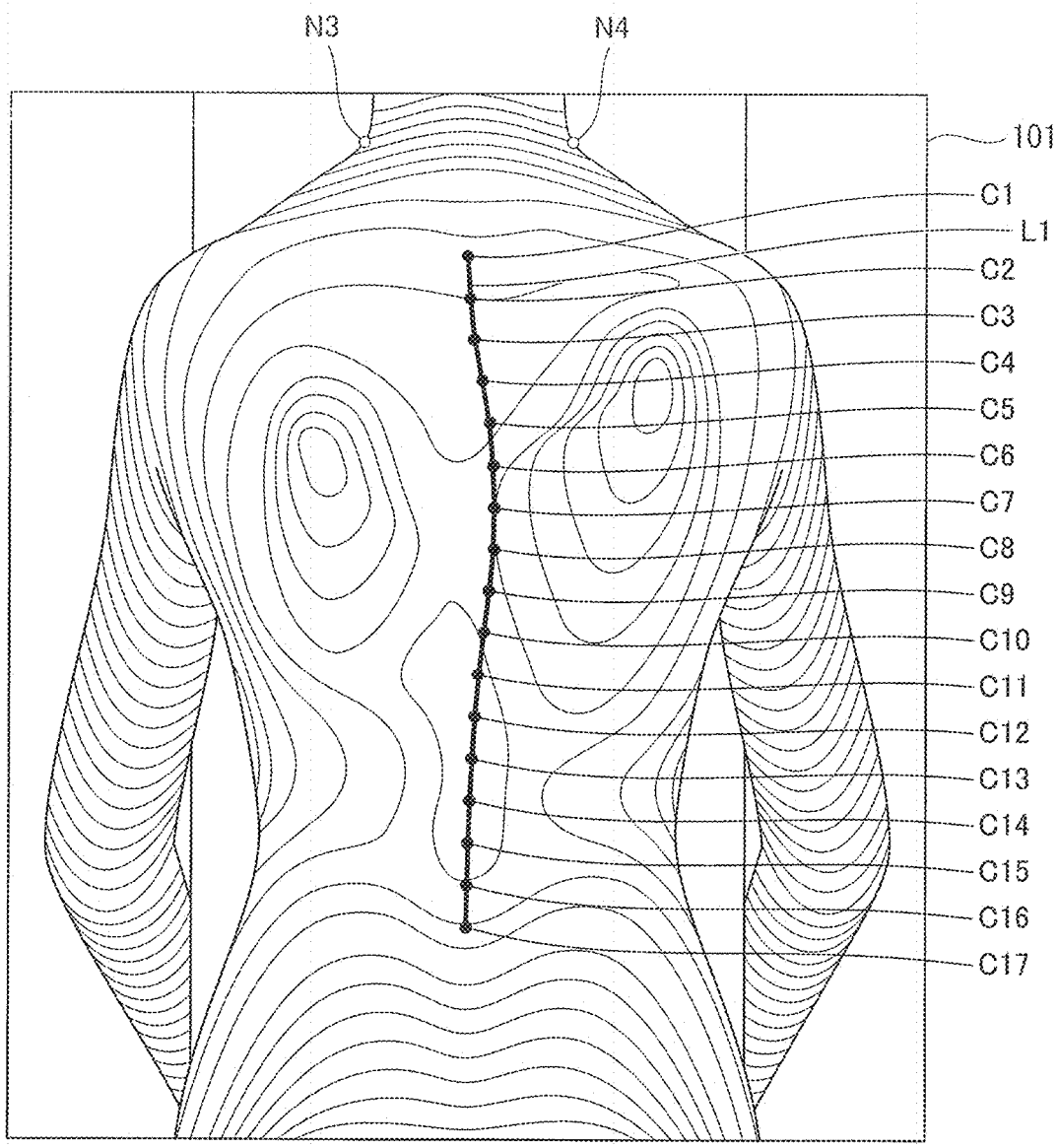
FIG. 9 is a schematic diagram illustrating an example of alignment between the moire image and the X-ray image according to the first embodiment of the present invention.

As a result, as illustrated in FIG. 9, the moire images 101 and the X-ray images 102 are aligned, and a coordinate system of the moire images 101 and a coordinate system of the X-ray images 102 are associated with each other. FIG. 9 illustrates a state in which the curve L1 corresponding to the centroids C1 to C17 of the thoracic vertebrae B1 to B12 and the lumbar vertebrae B13 to B17 on the X-ray images 102 illustrated in FIG. 8 is superimposed on the moire images 101. An alignment mark is not limited to two points of the base of the neck, and it is possible to adopt an anatomical feature point capable of aligning the moire images 101 and the X-ray images 102.

In FIG. 9, further, the SCAE unit 12 calculates coordinates $(X_{mi}, Y_{mi})$ (i=1 to 17) of the centroids C1 to C17 of the thoracic vertebrae B1 to B12 and the lumbar vertebrae B13 to B17 on the moire images 101 as correct answer data. The correct answer data of the calculated coordinates $(X_{mi}, Y_{mi})$ (i=1 to 17) of the centroids C1 to C17 on the moire images 101 is stored in the learning data memory 23. The processing of step S13 described above is performed for each data set of the large number of X-ray images stored in the X-ray image memory 21 and the large number of moire images stored in the learning image memory 22, and correct answer data calculated for each data set is stored in the learning data memory 23.

Subsequently, in step S14 of FIG. 5, the SCAE unit 12 performs machine learning so that arrangement information of the spinal-column elements is transferred when the moire images 101 is read from the learning image memory 22. Here, a description will be given of the case of adjusting a weight of the CNN implementing an algorithm of the SCAE unit 12.

Figure 10:
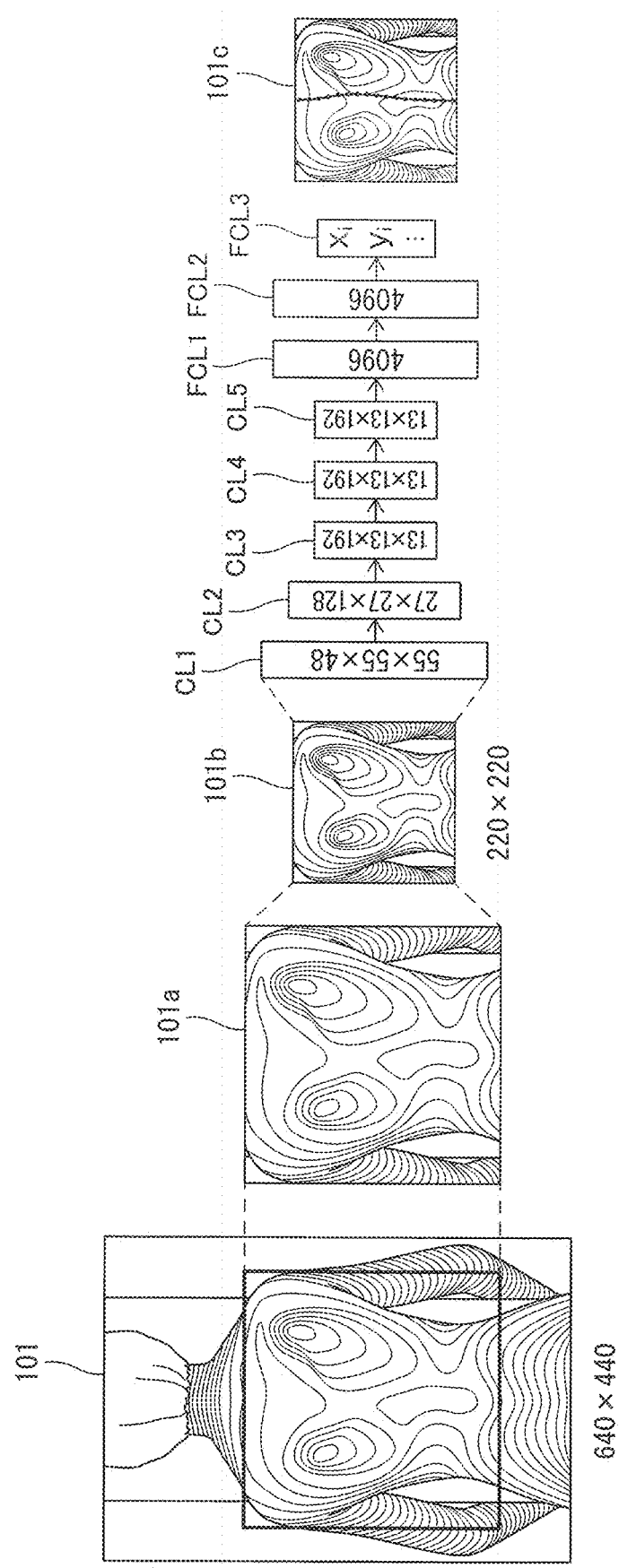
FIG. 10 is a schematic diagram illustrating an example of the machine learning method according to the first embodiment of the present invention.
Figure 11:
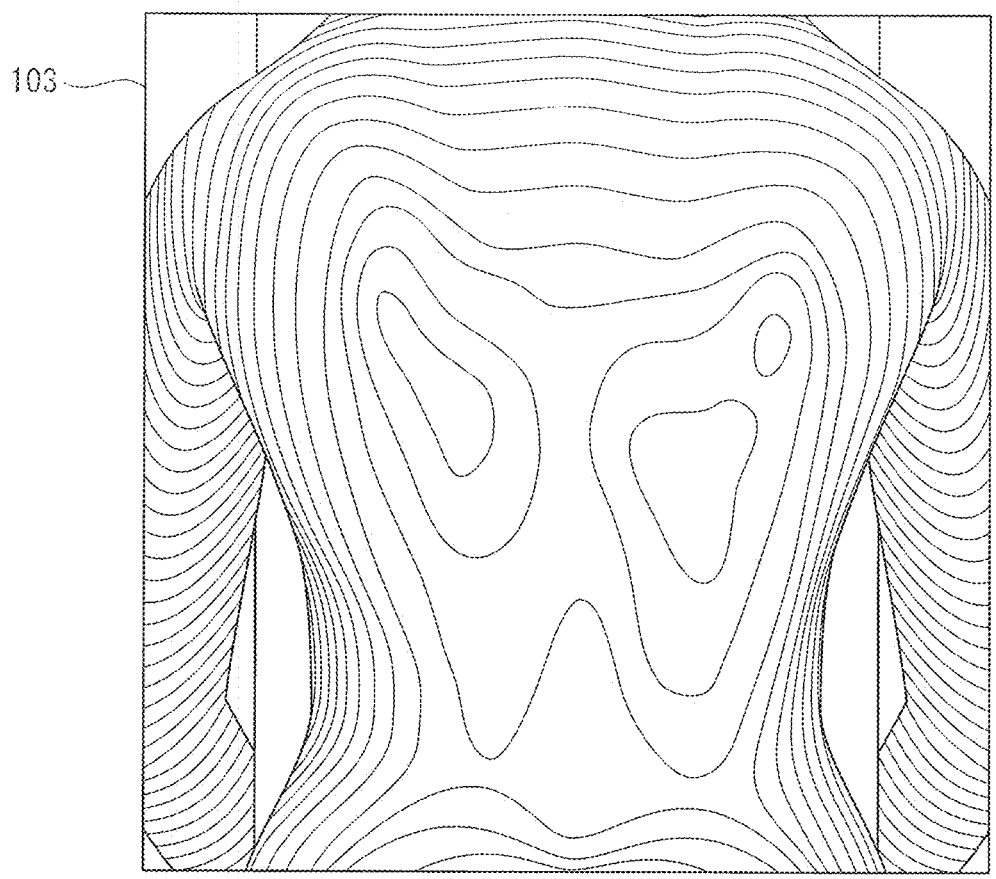
FIG. 11 is a schematic diagram illustrating an example of an unknown moire image according to the first embodiment of the present invention.

First, as illustrated in FIG. 10, for example, the SCAE unit 12 cuts out a part of the moire images 101 having 640×440 pixels read from the learning image memory 22 to obtain the moire images 101a. Further, the SCAE unit 12 resizes the moire images 101a to 220×220 pixels, and sets data of this resized moire images 101b as input data to a computer software program of the CNN. The data of the resized moire images 101b is input to the CNN program executed by the SCAE unit 12 at 256 gradations of gray scale without performing edge extraction, etc.

In the CNN executed by the SCAE unit 12 of the CPU 1, the algorithm of the network is configured such that the arrangement information of the spinal-column elements is transferred in response to input of the moire images 101b. As illustrated in FIG. 10, the CNN executed by the SCAE unit 12 has a learnable weight parameter, and constitutes a hierarchical network including, for example, five layers of convolution layers CL1 to CL5 performing feature extraction (filter processing) for each position on the image and, for example, three layers of total coupling layers FCL1 to FCL3 combining and identifying all units. Data of the convolution layers CL1 to CL5 and the total coupling layers FCL1 to FCL3 is successively stored in the learning data memory 23.

Although not illustrated, the CNN executed by the SCAE unit 12 has a free parameter, and may further have a pooling layer (partial sampling layer) that performs invariable output for local parallel translation and a local reaction normalization layer that locally normalizes an output. In the local reaction normalization layer, for example, processing is performed such that neighboring values are scanned to obtain sum of squares of the neighboring values and normalization is performed using a value obtained by linear transformation of the value.

A filter size of the convolution layer CL1 illustrated in FIG. 10 is 11×11, a filter size of the convolution layer CL2 is 5×5, and a filter size of each of the convolution layers CL3 to CL5 is 3×3. While gradually changing a scale, a local correlation pattern is extracted. The convolution layers CL 1 and CL 2 output data of 55×55×48 dimensions and data of 27×27×128 dimensions, respectively. Each of the convolution layers CL3 to CL5 output data of 13×13×192 dimensions. All coupling weights of the total coupling layer FCL1 to FCL3 are coupled to a unit of a previous layer, and each of the total coupling layers FCL1 and FCL2 outputs data of 4,096 dimensions. The last total coupling layer FCL3 is an output layer.

The CNN executed by the SCAE unit 12 calculates, as estimation data, coordinates $(X_{pi}, Y_{pi})$ (i=1 to 17) of the seventeen centroids C1 to C17 of the thoracic vertebrae B1 to B12 and the lumbar vertebrae B13 to B17 on the moire images 101c from the total coupling layer FCL3 located at a last stage of FIG. 1. The calculated coordinates $(X_{pi}, Y_{pi})$ (i=1 to 17) of the centroids C1 to C17 of the thoracic vertebrae B1 to B12 and the lumbar vertebrae B13 to B17 on the moire images 101c are stored in the learning data memory 23.

The SCAE unit 12 reads the coordinates $(X_{pi}, Y_{pi})$ (i=1 to 17) of the centroids C1 to C17 of the thoracic vertebrae B1 to B12 and the lumbar vertebrae B13 to B17 on the moire images 101c corresponding to the estimation data and the coordinates $(X_{mi}, Y_{mi})$ (i=1 to 17) of the centroids C1 to C17 of the thoracic vertebrae B1 to B12 and the lumbar vertebrae B13 to B17 on the moire images 101 corresponding to the correct answer data from the learning data memory 23, and calculates an error $(X_{pi}-X_{mi}, Y_{pi}-Y_{mi})$ (i=1 to 17) between the estimation data and the correct answer data for each of the centroids C1 to C17 of the thoracic vertebrae B1 to B12 and the lumbar vertebrae B13 to B17.

The SCAE unit 12 corrects weight parameters of the convolution layers CL1 to CL5 and the total coupling layers FCL1 to FCL3 of the CNN executed by the SCAE unit 12 to decrease the error $(X_{pi}-X_{mi}, Y_{pi}-Y_{mi})$ (i=1 to 17) using an error back propagation method (BP) with respect to the error $(X_{pi}-X_{mi}, Y_{pi}-Y_{mi})$ (i=1 to 17) between the estimation data and the correct answer data. In the error back propagation method, a weight is corrected by back propagating a gradient of the error from the total coupling layer FCL3 corresponding to an output layer to the convolution layer CL1 corresponding to an input layer. A gradient descent optimization method, etc. may be used in a learning algorithm of the error back propagation method for correcting this weight.

The SCAE unit 12 corrects weights by repeating processing of the error back propagation method described above using the data set of the large number of moire images and X-ray images stored in the learning image memory 22 and the X-ray image memory 21, thereby performing learning. As a result, the SCAE unit 12 may acquire an algorithm of the CNN for outputting the arrangement information of the spinal-column elements as learning data (accumulated data) when an unknown moire image is read from the learning image memory 22.

<Estimation Phase>

Next, a description will be given of a configuration and a function of the SCAE apparatus according to the first embodiment when the SCAE apparatus according to the first embodiment executes an estimation phase in which spinal-column arrangement is estimated from unknown moire images.

Figure 12:
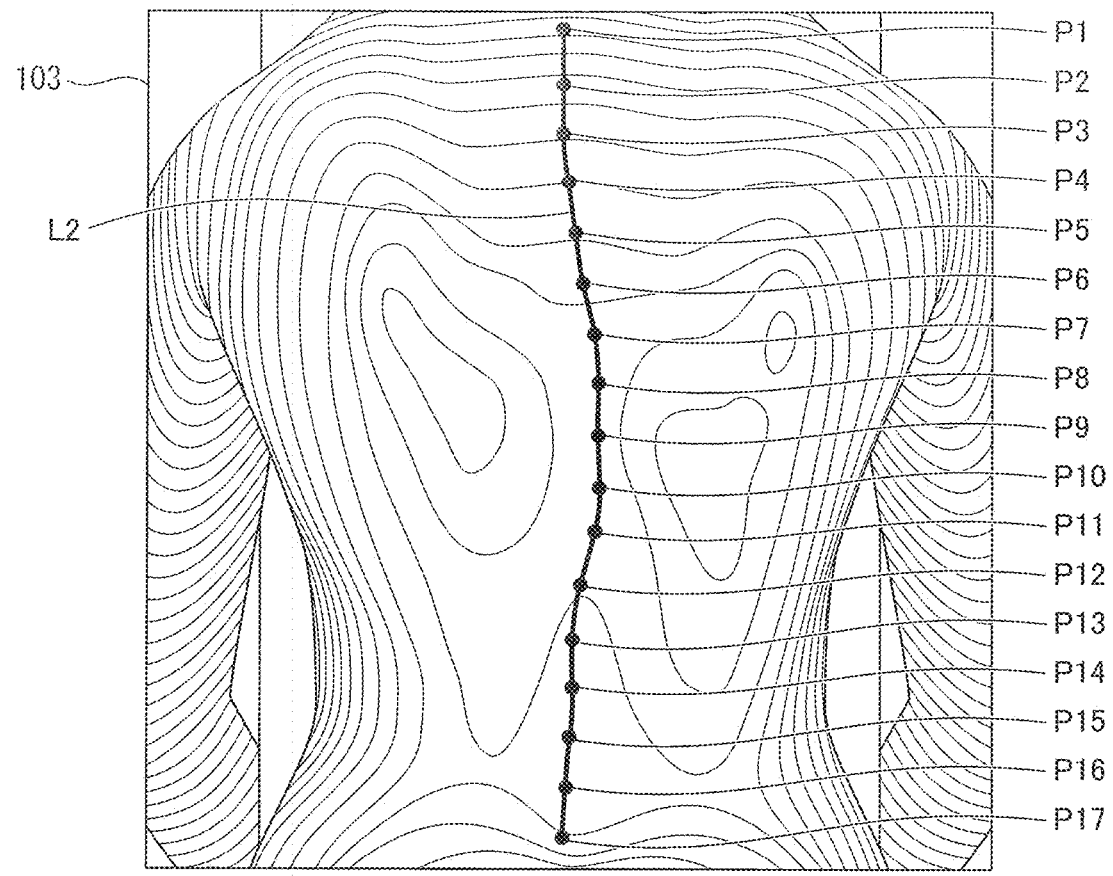
FIG. 12 is a schematic diagram illustrating an example of a moire image including an estimation result of spinal-column arrangement according to the first embodiment of the present invention.

The image acquisition unit 11 of the CPU 1 illustrated in FIG. 1 acquires unknown moire images 103 illustrated in FIG. 12, which are captured by the image sensor 3. The captured unknown moire images 103 are stored in the learning image memory 22. For example, as illustrated in FIG. 10, it is presumed that each of the moire images 103 includes 640×440 pixels and 256 gradations of gray scale.

The SCAE unit 12 of the CPU 1 executes the CNN performing machine learning through the learning phase described above. The SCAE unit 12 reads the moire images 103 stored in the learning image memory 22, and cuts out a part of the read moire images 103, respectively. Then, each of the cut moire images 103 is normalized by being resized to 220×220 pixels similarly to the time of machine learning illustrated in FIG. 10. The resized moire images 103 are stored in the estimation data memory 24.

Figure 13:
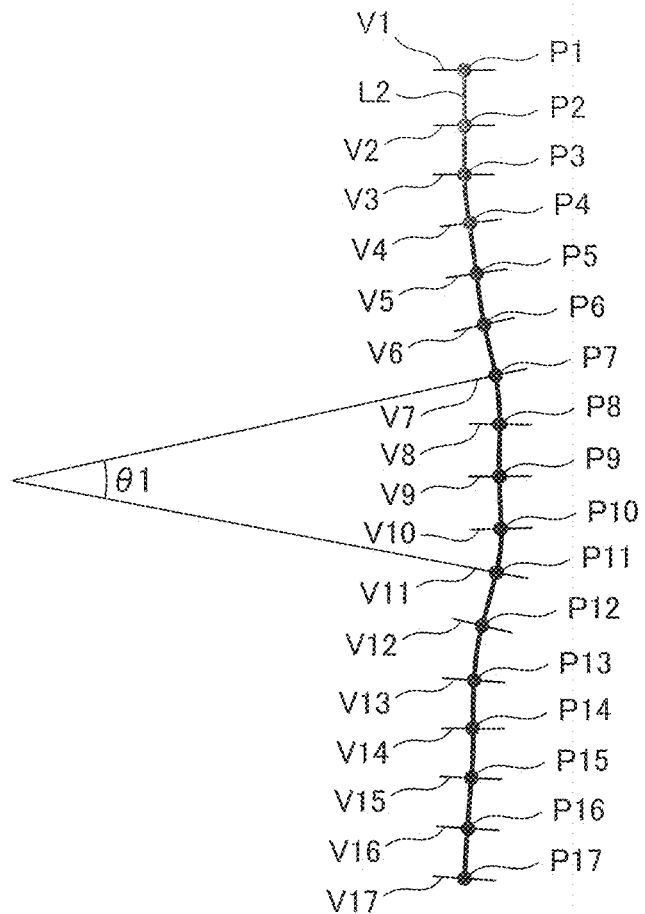
FIG. 13 is a schematic diagram for description of an example of a Cobb angle calculation method according to the first embodiment of the present invention.

The SCAE unit 12 reads the resized moire images 103 from the estimation data memory 24, and estimates, as spinal-column arrangement, coordinates $(x_{mi}, y_{mi})$ (i=1 to 17) of seventeen centroids P1 to P17 of the thoracic vertebrae B1 to B12 and the lumbar vertebrae B13 to B17 on the moire images 103 as illustrated in FIG. 13. The estimated coordinates $(x_{mi}, y_{mi})$ (i=1 to 17) of the centroids P1 to P17 on the moire images 103 are stored in the estimation data memory 24 as estimation data.

Further, the SCAE unit 12 calculates (estimates), as spinal-column arrangement, a curve L2 connecting the calculated coordinates $(x_{mi}, y_{mi})$ (i=1 to 17) of the centroids P1 to P17 of the thoracic vertebrae B1 to B12 and the lumbar vertebrae B13 to B17 on the moire images 103. For example, the curve L2 may correspond to a B-spline curve or a curve obtained by connecting adjacent centroids P1 to P17 using a straight line. The calculated curve L2 is stored in the estimation data memory 24 as estimation data.

The angle calculation unit 13 of the CPU 1 illustrated in FIG. 1 reads the coordinates $(x_{mi}, y_{mi})$ (i=1 to 17) of the centroids P1 to P17 of the thoracic vertebrae B1 to B12 and the lumbar vertebrae B13 to B17 on the moire images 103 and the curve L2 estimated by the SCAE unit 12 from the estimation data memory 24, and calculates a Cobb angle. The Cobb angle is defined as a turning angle of a spinal-column element by a Cobb method, and is a criterion for scoliosis. Straight extension lines are drawn from inclined horizontal planes of the upper and lower vertebral bodies (end vertebrae) whose horizontal planes are the most inclined in a curvature (curve) of targeted spinal-column arrangement, and the Cobb angle is calculated as an angle formed by the two extension lines. Present scoliosis treatment is mainly determined from a standing X-ray front image, and conservative treatment, brace treatment or surgery is selected according to a size of the Cobb angle in the standing X-ray front image.

For example, as illustrated in FIG. 13, the angle calculation unit 13 calculates vertical lines V1 to V17 perpendicular to the curve L2 and passing through the centroids P1 to P17 for each of the centroids P1 to P17 of the thoracic vertebrae B1 to B12 and the lumbar vertebrae B13 to B17 estimated by the SCAE unit 12 further, the angle calculation unit 13 extracts the thoracic vertebrae B7 and B11 corresponding to the vertical lines V7 and V11 having largest inclinations with respect to a horizontal direction as reference points (end vertebrae). Further, the angle calculation unit 13 calculates an angle formed by intersecting portions of the vertical lines V7 and V11 corresponding to the centroids P7 and P11 of the thoracic vertebrae B7 and B11 which are the reference points as a Cobb angle $\theta 1$. The calculated Cobb angle $\theta 1$ is stored in the estimation data memory 24.

As a method of calculating the Cobb angle $\theta 1$, it is possible to use vertical lines passing through upper ends or lower ends of the thoracic vertebrae B7 and B11, not the vertical lines V7 and V11 passing through the centroids P7 and P11 of the thoracic vertebrae B7 and B11 which are the reference points. In the first embodiment, since the centroids P7 and P11 of the thoracic vertebrae B7 and B11 are estimated, the vertical lines V7 and V11 are a substitute.

The image output control unit 14 of the CPU 1 illustrated in FIG. 1 reads the seventeen centroids P1 to P17 of the thoracic vertebrae B1 to B12 and the lumbar vertebrae B13 to B17 and the curve L2 estimated by the SCAE unit 12 from the estimation data memory 24, and outputs (displays) the centroids P1 to P17 of the thoracic vertebrae B1 to B12 and the lumbar vertebrae B13 to B17 and the curve L2 as an estimation result of arrangement information of the spinal-column elements to (on) a display, etc. included in the output device 4 so that the centroids P1 to P17 and the curve L2 are superimposed on the unknown moire images 103 as illustrated in FIG. 13.

Figure 14:
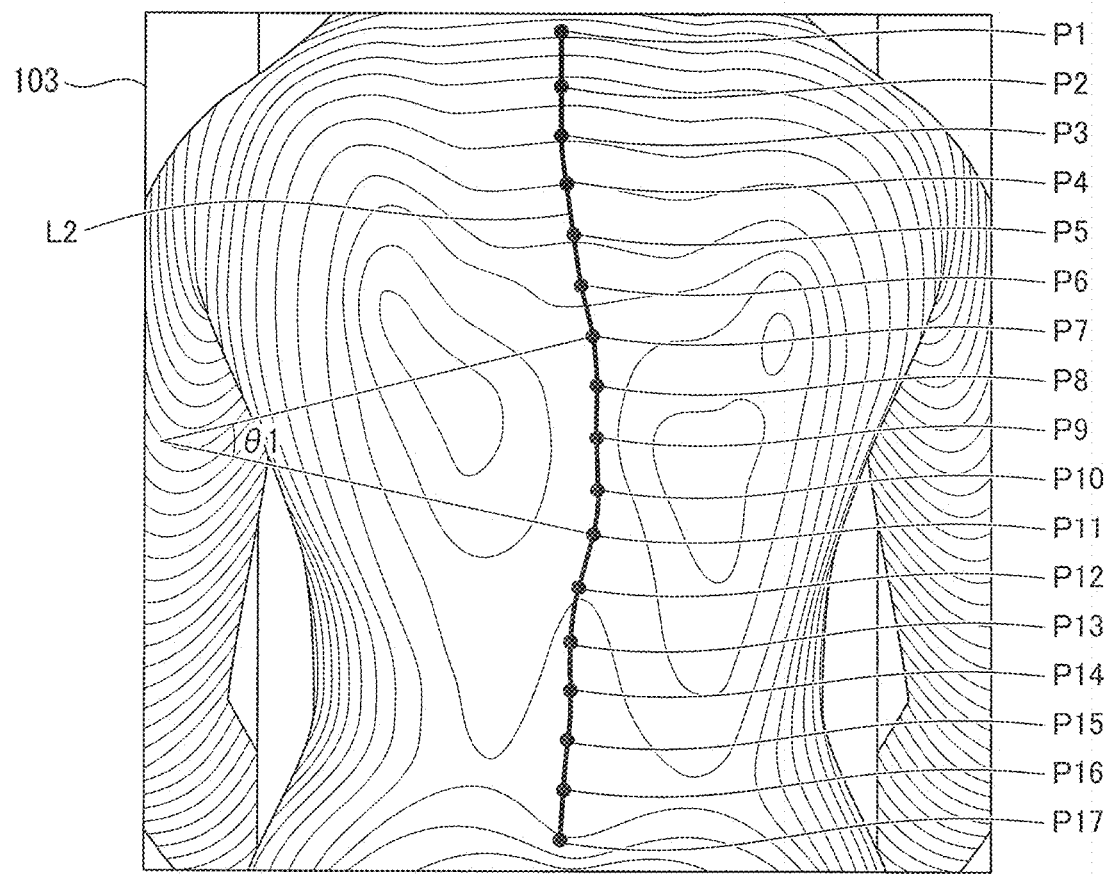
FIG. 14 is a schematic diagram illustrating an example of a moire image including an estimation result of spinal-column arrangement and a calculation result of a Cobb angle according to the first embodiment of the present invention.

Further, the image output control unit 14 may read the Cobb angle $\theta 1$ calculated by the angle calculation unit 13 from the estimation data memory 24, and output (display) the Cobb angle θ1 calculated by the angle calculation unit 13 together with the centroids P1 to P17 of the thoracic vertebrae B1 to B12 and the lumbar vertebrae B13 to B17 and the curve L2 estimated by the SCAE unit 12 on the moire images 103 to (on) the display, etc. included in the output device 4 as illustrated in FIG. 14. Referring to the Cobb angle θ1, a specific degree (numerical value) calculated by the angle calculation unit 13 may be output to (displayed on) the output device 4.

After calculating the Cobb angle θ1, the angle calculation unit 13 may determine whether the calculated Cobb angle θ1 is greater than or equal to a predetermined threshold value (for example, 20 degrees). A determination result of the Cobb angle θ1 is stored in the estimation data memory 24. Then, the image output control unit 14 may read the determination result of the Cobb angle θ1 from the estimation data memory 24, and output (display) the read determination result to (on) the display, etc. included in the output device 4.

In addition, in a case in which spinal-column arrangement corresponds to S-shaped scoliosis, two curves are present in one spinal-column arrangement. In this case, the angle calculation unit 13 may specify two end vertebrae for each of the two curves, and calculate the Cobb angle θ1. Calculation results of two Cobb angles θ1 are stored in the estimation data memory 24. Then, the image output control unit 14 may read the determination results of the two Cobb angles θ1 from the estimation data memory 24, and output (display) the read calculation results to (on) the display, etc. included in the output device 4.

<Spinal-Column Arrangement Estimation Method>

Next, a description will be given of an example of a spinal-column arrangement estimation method according to the first embodiment with reference to a flowchart of FIG. 15. The spinal-column arrangement estimation method shown below is merely an example, and the present invention is not limited to this procedure.

In step S21, the image sensor 3 captures the moire images. The captured unknown moire images are stored in the learning image memory 22 of the storage device 2. The unknown moire images may be stored in the learning image memory 22 of the storage device 2 in advance through an information network such as the Internet or an intranet not through the image sensor 3. Alternatively, an image acquired by a 3D scanner, etc. may be stored in the learning image memory 22 in advance through the image processor 10 that converts the moire images or 2D images equivalent to the moire images. The image acquisition unit 11 reads and acquires the unknown moire images from the learning image memory 22.

In step S22, the SCAE unit 12 of the CPU 1 estimates spinal-column arrangement from the unknown moire images acquired by the image acquisition unit 11 using the learning data (accumulated data) after machine learning stored in the learning data memory 23. An estimation result of the spinal-column arrangement is stored in the estimation data memory 24.

In step S23, the angle calculation unit 13 of the CPU 1 reads the spinal-column arrangement estimated by the SCAE unit 12 from the estimation data memory 24, and calculates a Cobb angle. The calculated Cobb angle is stored in the estimation data memory 24.

In step S24, the image output control unit 14 of the CPU 1 reads the spinal-column arrangement estimated by the SCAE unit 12 and the Cobb angle calculated by the angle calculation unit 13 from the estimation data memory 24, and displays the read spinal-column arrangement and Cobb angle on, for example, a screen of a display corresponding to the output device 4.

As described above, according to the SCAE apparatus and the spinal-column arrangement estimation method according to the first embodiment, it is possible to accurately estimate arrangement of spinal-column elements from the moire images using frameworks of AI with the CPU 1 using a machine learning scheme. Therefore, a doctor may accurately diagnose the presence or absence and a degree of scoliosis with reference to the estimated spinal-column arrangement and Cobb angle, and variation in diagnosis among doctors may be reduced. Determination of the presence or absence of side curvature becomes similarly easy for a determiner in a school checkup.

Further, since arrangement of spinal-column elements may be accurately estimated, it is possible to reduce implementation of basically unnecessary X-ray images such as a case in which scoliosis is suspected in the first checkup and scoliosis is denied by X-ray photography in the second checkup, and it is possible to reduce medical exposure of children, etc.

<SCAE Program>

Figure 15:
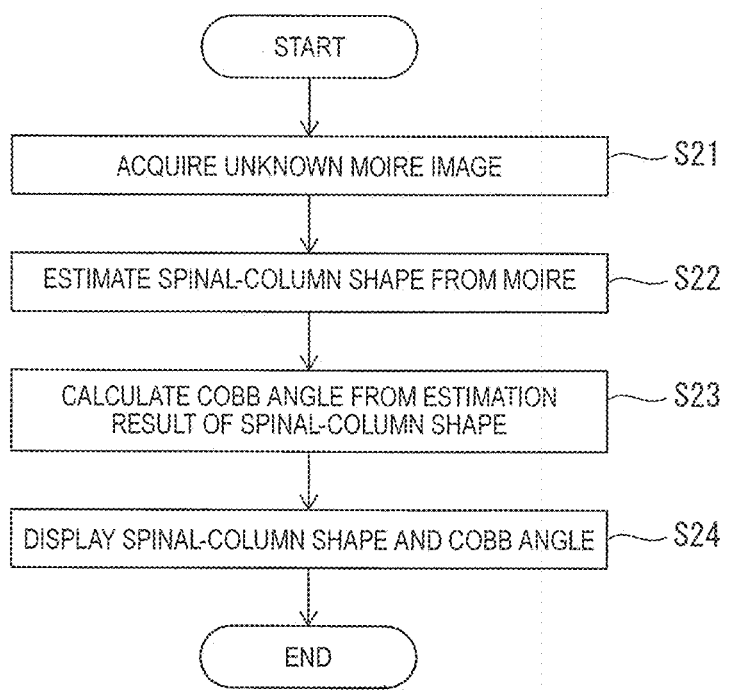
FIG. 15 is a flowchart for description of an example of a spinal-column arrangement estimation method according to the first embodiment of the present invention.

A SCAE program according to the first embodiment instructs the computer system, implementing the image processor 10, to execute the procedure of the spinal-column arrangement estimation method illustrated in FIG. 15. In more detail, the SCAE program according to the first embodiment instructs the computer system, implementing the image processor 10, to execute (a) an action configured to cause the image acquisition unit 11 to acquire images (moire images) representing a 3D shape of a human body surface on a back side, etc. of a human body, (b) an action configured to cause the SCAE unit 12 to estimate spinal-column arrangement of the human body from the acquired unknown moire images using learning data machine-learned from a data set of the moire images and X-ray images captured in the past, (c) an action configured to cause the angle calculation unit 13 to calculate a Cobb angle of the human body using the estimated spinal-column arrangement, (d) an action configured to cause the image output control unit 14 to output a signal for displaying the estimated spinal-column arrangement and the calculated Cobb angle on the output device 4, etc. For example, the SCAE program according to the first embodiment may be stored in the storage device 2.

Second Embodiment

In the first embodiment, a case in which spinal-column arrangement is two-dimensionally estimated has been illustrated. However, scoliosis is 3D deformation involving twisting of a spinal-column. For this reason, not only deformation (side curvature) viewed from a front but also deformation (front curvature and back curvature) viewed from a side or twisting (rotation) of a vertebral body are important factors in evaluation of scoliosis. Therefore, in a second embodiment of the present invention, a case in which spinal-column arrangement is three-dimensionally estimated will be illustrated.

<SCAE Apparatus>

Similarly to the SCAE apparatus according to the first embodiment, as illustrated in FIG. 1, the SCAE apparatus according to the second embodiment includes an image processor 10, an image sensor 3, and an output device 4. The second embodiment is different from the first embodiment in that the image sensor 3 is a 3D imaging machine that captures 3D images representing a 3D shape of a surface of a human body. For example, a 3D scanner may be used as the image sensor 3, and the image sensor 3 is not particularly limited as long as the device can capture the 3D images.

For example, the 3D scanner as the image sensor 3 captures the 3D images (range images) of a back of the human body by scanning the back of the human body. Alternatively, the 3D scanner as the image sensor 3 may capture 3D images of 360° including a front surface, a side surface, and a back surface of the human body by scanning the person while turning the person by 360° using a turn table. Then, data on the back side of the human body may be selectively used from the 3D images of 360°.

For example, the image sensor 3 captures the 3D images 201 of the human body surface schematically illustrated in FIG. 16A and FIG. 16B. FIG. 16A illustrates a 3D image 201 viewed from the back surface side of the human body, and FIG. 16B illustrates the 3D image 201 on the back side when the human body is viewed from the side surface side in a direction different by 90° from FIG. 16A. As illustrated in FIG. 16A and FIG. 16B, the 3D image 201 includes 3D information in an x-axis direction corresponding to a left-right direction, a y-axis direction corresponding to a vertical direction, and a z-axis direction corresponding to a depth direction when viewed from the back surface of the human body. In FIG. 16A and FIG. 16B, hatching is schematically distinguished in stages according to a distance between the image sensor 3 in the z-axis direction and the back surface of the human body. In the case of a scoliosis patient, in particular, a difference of elevation of the back of the human body is large between left and right sides, and a distribution of the distance in the z-axis direction is asymmetric between the left and right sides.

<Learning Phase>

Here, a description will be given of an example of a "learning phase" including a machine learning method of a SCAE unit 12 according to the second embodiment with reference to a flowchart of FIG. 17. Here, a case in which the SCAE unit 12 includes a CNN will be illustrated.

As an advanced preparation for the machine learning by the SCAE unit 12, in step S31, a large number of data sets (for example, thousands of sets) of 3D images representing 3D shapes of the back surface of the human body captured for the same person etc. in the past, and X-ray images corresponding to the 3D images captured in the past, are prepared. Each of the large number of 3D images and X-ray images is stored in a learning image memory 22 and an X-ray image memory 21 of a storage device 2.

For example, a large number of sets of 3D images 201, one (set) of which is illustrated in FIG. 16A and FIG. 16B, are stored in the learning image memory 22, and a large number of sets of CT images 202 as X-ray images, one (set) of which is illustrated in FIG. 18A to FIG. 18C, are stored in the X-ray image memory 21. The CT images 202 are captured in a supine position. FIG. 18A illustrates a CT image 202 of a specific cross section when the human body is viewed from the back surface side, FIG. 18B illustrates a CT image 202 of a specific cross section when the human body is viewed from the side surface side, and FIG. 18C illustrates a CT image 202 of a specific cross section when the human body is viewed from an upper side. As illustrated in FIG. 18A to FIG. 18C, the CT image 202 includes 3D voxel data in the x-axis direction corresponding to the left-right direction, the y-axis direction corresponding to the vertical direction, and the z-axis direction corresponding to the depth direction when viewed from the back surface of the human body.

Subsequently, in step S32 of FIG. 17, labeling of correct answer data used for machine learning is performed. The SCAE unit 12 reads one (one set of) CT image 202 from the X-ray image memory 21, and calculates 3D coordinates of a centroid of a spinal-column element on the CT image 202 using an anatomical feature point. For example, as illustrated in FIG. 18A to FIG. 18C, each of lumbar vertebrae B14 viewed from the front surface (z-axis direction) and the side surface (x-axis direction) of the human body is rectangle-approximated, and coordinates $(X_{ct14}, Y_{ct14}, Z_{ct14})$ of a centroid C14 of the lumbar vertebra B14 on the CT image 202 is calculated. Similarly to the lumbar vertebra B14, for the other thoracic vertebrae B1 to B12 and lumbar vertebrae B13, B15 to B17, the thoracic vertebrae B1 to B12 and the lumbar vertebrae B13, B15 to B17 are extracted from voxel data of the CT image 202, and coordinates $(X_{cti}, Y_{cti}, Z_{cti})$ (i=1 to 17) of centroids C1 to C13 and C15 to C17 of the thoracic vertebrae B1 to B12 and the lumbar vertebrae B13, B15 to B17 on the CT image 202 are calculated. The calculated coordinates $(X_{cti}, Y_{cti}, Z_{cti})$ (i=1 to 17) of the centroids C1 to C17 on the CT image 202 are stored in a learning data memory 23.

Subsequently, in step S33 of FIG. 17, the SCAE unit 12 reads the 3D images 201 and the CT images 202 corresponding to a data set from the learning image memory 22 and the X-ray image memory 21, respectively, and three-dimensionally aligns the 3D images 201 and the CT images 202. For example, for each of the 3D images 201 and the CT images 202, feature points such as positions of left and right bases of a neck of the human body viewed from the front surface (z-axis direction) of the human body, a position of a base of the neck on the back surface side viewed from the side surface (x-axis direction) of the human body, etc. are extracted as alignment marks, respectively.

Then, sizes of the 3D images 201 and the CT images 202 are adjusted, and rotation, parallel translation, etc. of the 3D images 201 and the CT images 202 are performed so that the respective alignment marks of the 3D images 201 and the CT images 202 coincide with each other. As a result, the 3D images 201 and the CT images 202 will three-dimensionally overlap each other, and a coordinate system of the 3D images 201 and a coordinate system of the CT images 202 are associated with each other.

Further, the SCAE unit 12 calculates coordinates $(X_{3di}, Y_{3di}, Z_{3di})$ (i=1 to 17) of the centroids C1 to C17 of the thoracic vertebrae B1 to B12 and the lumbar vertebrae B13 to B17 on the 3D images 201 as correct answer data. The correct answer data corresponding to the calculated coordinates $(X_{3di}, Y_{3di}, Z_{3di})$ (i=1 to 17) of the centroids C1 to C17 on the 3D images 201 is stored in the learning data memory 23. The processing of step S33 described above is performed for each data set of the large number of CT images stored in the X-ray image memory 21 and the large number of 3D images stored in the learning image memory 22, and correct answer data calculated for each data set is stored in the learning data memory 23.

Subsequently, in step S34 of FIG. 17, similarly to the first embodiment, the SCAE unit 12 performs machine learning so that arrangement information of the spinal-column elements is transferred when the 3D images 201 is read from the learning image memory 22. For example, the SCAE unit 12 cuts out and resizes a part of the 3D images 201 read from the learning image memory 22, and sets data of this resized 3D image 201 as input data to a computer software program of the CNN.

In the CNN executed by the SCAE unit 12 of the CPU 1, a network algorithm is configured such that 3D arrangement information of spinal-column elements is provided in response to input of the resized 3D image 201. The CNN executed by the SCAE unit 12 calculates coordinates ($X_{pi}$, $Y_{pi}$, $Z_{pi}$) (i=1 to 17) of the seventeen centroids C1 to C17 of the thoracic vertebrae B1 to B12 and the lumbar vertebrae B13 to B17 on the 3D images 201 as estimation data. The calculated coordinates ($X_{pi}$, $Y_{pi}$, $Z_{pi}$) (i=1 to 17) of the centroids C1 to C17 of the thoracic vertebrae B1 to B12 and the lumbar vertebrae B13 to B17 on the 3D images 201 are stored in the learning data memory 23.

The SCAE unit 12 reads the coordinates ($X_{pi}$, $Y_{pi}$, $Z_{pi}$) (i=1 to 17) of the centroids C1 to C17 of the thoracic vertebrae B1 to B12 and the lumbar vertebrae B13 to B17 on the 3D images 201 corresponding to the estimation data and the coordinates ($X_{3di}$, $Y_{3di}$, $Z_{3di}$) (i=1 to 17) of the centroids C1 to C17 of the thoracic vertebrae B1 to B12 and the lumbar vertebrae B13 to B17 on the 3D images 201 corresponding to the correct answer data from the learning data memory 23, and calculates an error ($X_{pi}-X_{3di}$, $Y_{pi}-Y_{3di}$, $Z_{pi}-Z_{3di}$) (i=1 to 17) between the estimation data and the correct answer data for each of the centroids C1 to C17 of the thoracic vertebrae B1 to B12 and the lumbar vertebrae B13 to B17. The error ($X_{pi}-X_{3di}$, $Y_{pi}-Y_{3di}$, $Z_{pi}-Z_{3di}$) (i=1 to 17) between the estimation data and the correct answer data is stored in the learning data memory 23.

The SCAE unit 12 reads the error ($X_{pi}-X_{3di}$, $Y_{pi}-Y_{3di}$, $Z_{pi}-Z_{3di}$) (i=1 to 17) between the estimation data and the correct answer data from the learning data memory 23, and corrects a weight parameter to decrease the error ($X_{pi}-X_{3di}$, $Y_{pi}-Y_{3di}$, $Z_{pi}-Z_{3di}$) (i=1 to 17) between the estimation data and the correct answer data using the error back propagation method (BP).

The SCAE unit 12 corrects weights by repeating processing of the error back propagation method described above using the data set of the large number of 3D images and CT images stored in the learning image memory 22 and the X-ray image memory 21, thereby performing learning. As a result, the SCAE unit 12 may acquire an algorithm of the CNN as learning data (accumulated data) for outputting the arrangement information of the spinal-column elements when an unknown 3D image is read from the learning image memory 22.

<Estimation Phase>

Next, a description will be given of a configuration and a function of the SCAE apparatus according to the second embodiment when the SCAE apparatus pertaining to the second embodiment executes an estimation phase, in which spinal-column arrangement is estimated from an unknown 3D image.

Figure 19A:
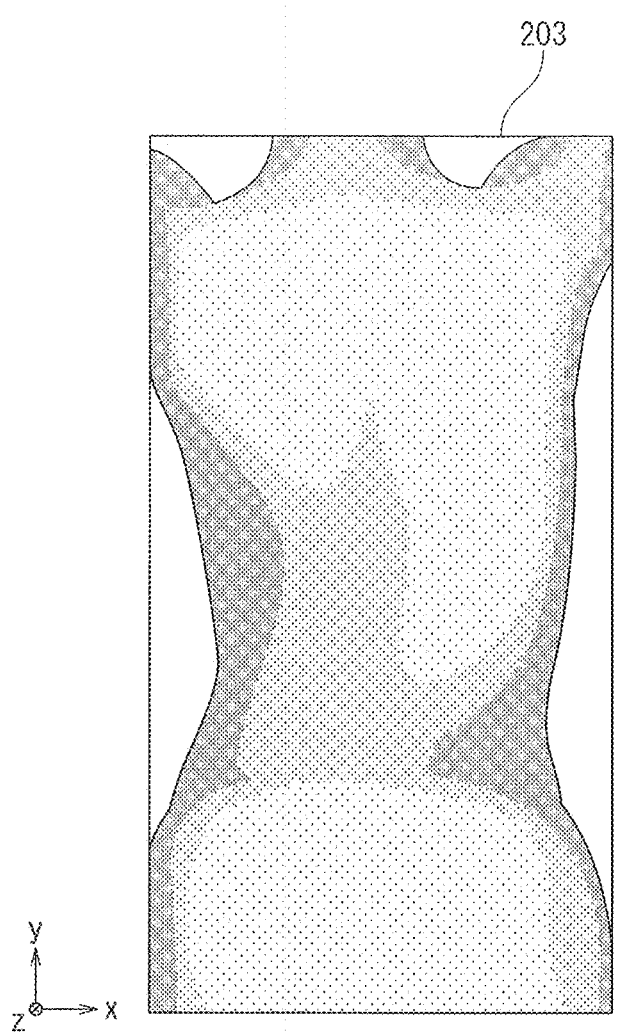
FIG. 19A and FIG. 19B are schematic diagrams illustrating an example of an unknown 3D image according to the second embodiment of the present invention when viewed from different directions, respectively.
Figure 19B:
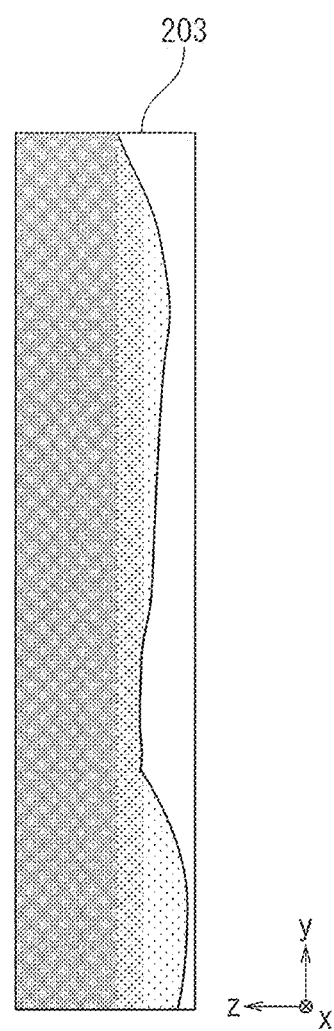

An image acquisition unit 11 of the CPU 1 illustrated in FIG. 1 acquires an unknown 3D image 203 illustrated in FIG. 19A and FIG. 19B captured by the image sensor 3. FIG. 19A illustrates a 3D image 203 viewed from the back surface side of the human body, and FIG. 19B illustrates a 3D image 203 on the back side when the human body is viewed from the side surface side in a direction different by 90° from FIG. 19A. The acquired unknown 3D images 203 are stored in the learning image memory 22.

The SCAE unit 12 of the CPU 1 executes the CNN performing machine learning through the learning phase described above. The SCAE unit 12 reads the 3D images 203 stored in the learning image memory 22, and cuts out a part of the read 3D image 203. Then, the cut 3D image 203 is normalized by being resized to the same size as that at the time of machine learning. The resized 3D image 203 is stored in an estimation data memory 24.

The SCAE unit 12 reads the resized 3D image 203 from the estimation data memory 24, and estimates coordinates ($x_{3di}$, $y_{3di}$, $z_{3di}$) (i=1 to 17) of seventeen centroids P1 to P17 of the thoracic vertebrae B1 to B12 and the lumbar vertebrae B13 to B17 on the 3D images 203 as spinal-column arrangement as illustrated in FIG. 20A and FIG. 20B. The estimated coordinates ($x_{3di}$, $y_{3di}$, $z_{3di}$) (i=1 to 17) of the centroids P1 to P17 on the 3D images 203 are stored in the estimation data memory 24 as estimation data.

Further, the SCAE unit 12 calculates (estimates) a 3D curve L3 connecting the calculated coordinates ($x_{3di}$, $y_{3di}$, $z_{3di}$) (i=1 to 17) of the centroids P1 to P17 of the thoracic vertebrae B1 to B12 and the lumbar vertebrae B13 to B17 on the 3D images 203 as spinal-column arrangement. For example, the curve L3 may correspond to a B-spline curve or a curve obtained by connecting adjacent centroids P1 to P17 using a straight line. The calculated curve L3 is stored in the estimation data memory 24 as estimation data.

An angle calculation unit 13 of the CPU 1 illustrated in FIG. 1 reads the coordinates ($x_{3di}$, $y_{3di}$, $z_{3di}$) (i=1 to 17) of the centroids P1 to P17 of the thoracic vertebrae B1 to B12 and the lumbar vertebrae B13 to B17 on the 3D images 203 and the curve L3 estimated by the SCAE unit 12 from the estimation data memory 24, and calculates a Cobb angle θ2 using the same scheme as that of the first embodiment. In the second embodiment, since the coordinates ($x_{3di}$, $y_{3di}$, $z_{3di}$) (i=1 to 17) of the centroids P1 to P17 of the thoracic vertebrae B1 to B12 and the lumbar vertebrae B13 to B17 on the 3D images 203 and the curve L3 are three-dimensionally calculated, the Cobb angle θ2 is three-dimensionally calculated. The calculated Cobb angle θ2 is stored in the estimation data memory 24.

An image output control unit 14 of the CPU 1 illustrated in FIG. 1 reads the coordinates ($x_{3di}$, $y_{3di}$, $z_{3di}$) (i=1 to 17) of the seventeen centroids P1 to P17 of the thoracic vertebrae B1 to B12 and the lumbar vertebrae B13 to B17 on the 3D images 203 and the curve L3 estimated by the SCAE unit 12 from the estimation data memory 24, and outputs (displays) the coordinates ($x_{3di}$, $y_{3di}$, $z_{3di}$) (i=1 to 17) of the centroids P1 to P17 of the thoracic vertebrae B1 to B12 and the lumbar vertebrae B13 to B17 on the 3D images 203 and the curve L3 as an estimation result of arrangement information of spinal-column elements to (on) a display, etc. included in the output device 4 so that the centroids P1 to P17 and the curve L3 are superimposed on the unknown 3D image 203 as illustrated in FIG. 20A and FIG. 20B.

Further, the image output control unit 14 may read the Cobb angle θ2 calculated by the angle calculation unit 13 from the estimation data memory 24, and output (display) the Cobb angle θ2 together with the centroids P1 to P17 of the thoracic vertebrae B1 to B12 and the lumbar vertebrae B13 to B17 and the curve L3 estimated by the SCAE unit 12 to (on) the display, etc. included in the output device 4 so that the Cobb angle θ2, the centroids P1 to P17, and the curve L3 are superimposed on the 3D images 203 as illustrated in FIG. 20A and FIG. 20B.

<Spinal-Column Arrangement Estimation Method>

Next, a description will be given of an example of a spinal-column arrangement estimation (SCAE) method according to the second embodiment with reference to a flowchart of FIG. 21. The SCAE method shown below is merely an example, and the present invention is not limited to this procedure.

In step S41, the image sensor 3 captures 3D images representing a 3D shape of a human body surface. The captured unknown 3D images are stored in the learning image memory 22 of the storage device 2. By the way, unknown 3D images may not be images captured by the image sensor 3, but the unknown 3D images may be obtained through an information network such as the Internet or an intranet, and the unknown 3D images obtained through an information network may be stored in the learning image memory 22 of the storage device 2 in advance. In addition, the unknown 3D images may not be specific images captured by the same 3D imaging machine, which is the same machine when a data set of the 3D images for machine learning is obtained, but may be any 3D images that can represent the 3D shape of the human body surface. The image acquisition unit 11 reads and acquires the unknown 3D image from the learning image memory 22.

In step S42, the SCAE unit 12 of the CPU 1 estimates spinal-column arrangement from the unknown 3D image acquired by the image acquisition unit 11 using learning data (accumulated data) after machine learning stored in the learning data memory 23. An estimation result of the spinal-column arrangement is stored in the estimation data memory 24.

In step S43, the angle calculation unit 13 of the CPU 1 reads the spinal-column arrangement estimated by the SCAE unit 12 from the estimation data memory 24 to calculate a Cobb angle. The calculated Cobb angle is stored in the estimation data memory 24.

In step S44, the image output control unit 14 of the CPU 1 reads the spinal-column arrangement estimated by the SCAE unit 12 and the Cobb angle calculated by the angle calculation unit 13 from the estimation data memory 24, and displays the read spinal-column arrangement and Cobb angle on, for example, a screen of a display corresponding to the output device 4.

As described above, according to the SCAE apparatus and the SCAE method pertaining to the second embodiment, similarly to the first embodiment, it is possible to accurately estimate arrangement of spinal-column elements from 3D images using frameworks of AI with the CPU 1 using a machine learning scheme. Therefore, a doctor may accurately diagnose the presence or absence and a degree of scoliosis with reference to the estimated spinal-column arrangement and Cobb angle, and variation in diagnosis among doctors may be reduced.

Furthermore, according to the SCAE apparatus and the SCAE method pertaining to the second embodiment, it is possible to estimate 3D arrangement of spinal-column elements from 3D images, using learning data obtained by 3D images and CT images as a data set, and it is possible to calculate a 3D maximum Cobb angle. Therefore, it is possible to more accurately estimate spinal-column arrangement and a Cobb angle.

In addition, because commercial production of the moire images pickup machine has been discontinued, and a new SCAE apparatus not using the moire image pickup machine is needed. On the other hand, since arrangement of spinal-column elements may be three-dimensionally estimated from 3D images captured by the 3D imaging machine, use as a new SCAE apparatus may be expected.

<SCAE Program>

Figure 21:
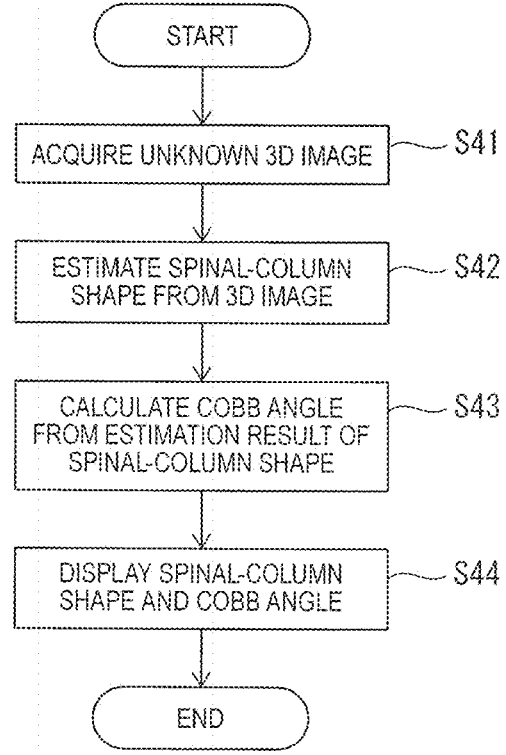
FIG. 21 is a flowchart for description of an example of a spinal-column arrangement estimation method according to the second embodiment of the present invention.

A SCAE program according to the second embodiment instructs the computer system, implementing the image processor 10, to execute the sequence of the procedures along the SCAE method illustrated in FIG. 21. In more detail, the SCAE program according to the second embodiment instructs the computer system, implementing the image processor 10, to execute (a) an action configured to cause the image acquisition unit 11 to acquire an unknown 3D image representing a 3D shape of a human body surface, (b) an action configured to cause the SCAE unit 12 to estimate spinal-column arrangement of the human body from the acquired unknown 3D image using learning data machine-learned from a data set of 3D images and X-ray images (CT image) captured in the past, (c) an action configured to cause the angle calculation unit 13 to calculate a Cobb angle of the human body using the estimated spinal-column arrangement, (d) an action configured to cause the image output control unit 14 to output a signal for displaying the estimated spinal-column arrangement and the calculated Cobb angle on the output device 4, etc. For example, the SCAE program according to the second embodiment may be stored in the storage device 2.

(Modification of Second Embodiment)

As a modification of the second embodiment, a case in which twisting (rotation) of a vertebra is estimated is illustrated. Evaluation of scoliosis is performed mainly by standing X-ray images (front surface images and side surface images) and CT images. Specifically, deformation (side curvature) viewed from a front is evaluated using the standing X-ray front surface images, and a front curvature or a back curvature is evaluated using the standing X-ray side surface images. With regard to rotation, a degree of rotation is evaluated from appearance of the vertebra on the standing X-ray front surface image using a Nash & Moe method, etc. However, an angle of rotation is not directly evaluated. On the other hand, in the CT images, rotation of the vertebra is directly evaluated. However, normally, exposure is greater than that at the time of capturing the X-ray images. Since most of scoliosis cases correspond to children, there is a possibility of future health damage. In contrast, in the modification of the second embodiment, rotation of the vertebra is accurately estimated without capturing CT images.

<Learning Phase>

As an advanced preparation for the machine learning by the SCAE unit 12, in step S31 of a learning phase illustrated in FIG. 17, a large number of data sets (for example, thousands of sets) of 3D images representing a 3D shape of a back surface of the human body, which are captured in the past, and X-ray images (CT images) corresponding to the 3D images captured in the past, are prepared. Each of a large number of 3D images and X-ray images is stored in the learning image memory 22 and the X-ray image memory 21 of the storage device 2.

Figure 22A:
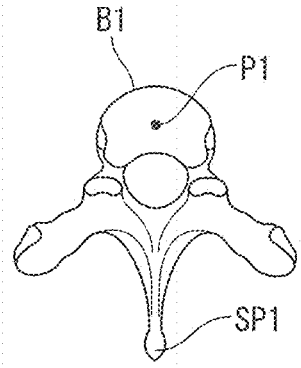
FIG. 22A is a top view illustrating an example of a vertebral body according to a modification of the second embodiment of the present invention.
Figure 22B:
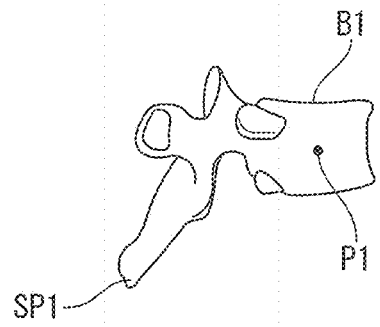
FIG. 22B is a side view illustrating the example of the vertebral body obtained by viewing FIG. 22A from a direction different by 90°.

Subsequently, in step S32 of FIG. 17, labeling of correct answer data used for machine learning is performed. The SCAE unit 12 calculates coordinates $(X_{cti}, Y_{cti}, Z_{cti})$ (i=1 to 17) of seventeen centroids C1 to C17 of the thoracic vertebrae B1 to B12 and the lumbar vertebrae B13 to B17 on CT images 202 from the CT images 202, and calculates 3D coordinates of a spinous process of each of the thoracic vertebrae B1 to B12 and the lumbar vertebrae B13 to B17. For example, as illustrated in FIG. 22A and FIG. 22B, a spinous process SP1 refers to a portion at which a rear end of the vertebra (thoracic vertebra) B1 rises and protrudes. The spinous process SP1 can be specified as a feature point from the CT images 202. The SCAE unit 12 calculates 3D coordinates $(X_{sp1}, Y_{sp1}, Z_{sp1})$ of the spinous process SP1 of the thoracic vertebra B1 on the CT images 202. Although not illustrated, it is possible to similarly calculate 3D coordinates $(X_{ctspi}, Y_{ctspi}, Z_{ctspi})$ (i=2 to 17) of spinous processes SP2 to SP17 of the other thoracic vertebrae B2 to B12 and lumbar vertebrae B13 to B17 on the CT images 202. The calculated coordinates $(X_{cti}, Y_{cti}, Z_{cti})$ (i=1 to 17) of the centroids C1 to C17 on the CT images 202 and 3D coordinates $(X_{ctspi}, Y_{ctspi}, Z_{ctspi})$ (i=1 to 17) of the spinous processes SP1 to SP17 of the thoracic vertebrae B1 to B12 and the lumbar vertebrae B13 to B17 on the CT images 202 are stored in the learning data memory 23.

Subsequently, in step S33 of FIG. 17, the SCAE unit 12 reads the 3D images 201 and the CT images 202 corresponding to a data set from the learning image memory 22 and the X-ray image memory 21, respectively, three-dimensionally aligns the 3D images 201 and the CT images 202, and associates a coordinate system of the 3D images 201 and a coordinate system of the CT images 202 with each other.

Further, the SCAE unit 12 calculates coordinates $(X_{3di}, Y_{3di}, Z_{3di})$ (i=1 to 17) of the centroids C1 to C17 of the thoracic vertebrae B1 to B12 and the lumbar vertebrae B13 to B17 on the 3D images 201 as correct answer data. The correction answer data corresponding to the calculated coordinates $(X_{3di}, Y_{3di}, Z_{3di})$ (i=1 to 17) of the centroids C1 to C17 on the 3D images 201 is stored in the learning data memory 23. Further the SCAE unit 12 calculates 3D coordinates $(X_{3dspi}, Y_{3dspi}, Z_{3dspi})$ (i=1 to 17) of the spinous processes SP1 to SP17 of the thoracic vertebrae B1 to B12 and the lumbar vertebrae B13 to B17 on the 3D images 201 as correct answer data. The correct answer data corresponding to the calculated 3D coordinates $(X_{3dspi}, Y_{3dspi}, Z_{3dspi})$ (i=1 to 17) of the centroids C1 to C17 on the 3D images 201 is stored in the learning data memory 23. The processing of step S33 described above is performed for each data set of the large number of CT images stored in the X-ray image memory 21 and the large number of 3D images stored in the learning image memory 22, and correct answer data calculated for each data set is stored in the learning data memory 23.

Subsequently, in step S34 of FIG. 17, the SCAE unit 12 performs machine learning such that when the 3D images 201 is read from the learning image memory 22, 3D coordinates $(X_{spi}, Y_{spi}, Z_{spi})$ (i=1 to 17) of the seventeen spinous processes SP1 to SP17 of the thoracic vertebrae B1 to B12 and the lumbar vertebrae B13 to B17 on the 3D images 201 are output in addition to coordinates $(X_{pi}, Y_{pi}, Z_{pi})$ (i=1 to 17) of the seventeen centroids C1 to C17 of the thoracic vertebrae B1 to B12 and the lumbar vertebrae B13 to B17 on the 3D images 201.

The CNN executed by the SCAE unit 12 calculates the coordinates $(X_{pi}, Y_{pi}, Z_{pi})$ (i=1 to 17) of the seventeen centroids C1 to C17 of the thoracic vertebrae B1 to B12 and the lumbar vertebrae B13 to B17 on the 3D images 201 and the 3D coordinates $(X_{spi}, Y_{spi}, Z_{spi})$ (i=1 to 17) of the seventeen spinous processes SP1 to SP17 of the thoracic vertebrae B1 to B12 and the lumbar vertebrae B13 to B17 on the 3D images 201 as estimation data. The calculated coordinates $(X_{pi}, Y_{pi}, Z_{pi})$ (i=1 to 17) of the centroids C1 to C17 of the thoracic vertebrae B1 to B12 and the lumbar vertebrae B13 to B17 on the 3D images 201 and 3D coordinates $(X_{spi}, Y_{spi}, Z_{spi})$ (i=1 to 17) of the spinous processes SP1 to SP17 of the thoracic vertebrae B1 to B12 and the lumbar vertebrae B13 to B17 on the 3D images 201 are stored in the learning data memory 23.

The SCAE unit 12 reads the coordinates $(X_{pi}, Y_{pi}, Z_{pi})$ (i=1 to 17) of the centroids C1 to C17 of the thoracic vertebrae B1 to B12 and the lumbar vertebrae B13 to B17 on the 3D images 201 and the 3D coordinates $(X_{spi}, Y_{spi}, Z_{spi})$ (i=1 to 17) of the spinous processes SP1 to SP17 of the thoracic vertebrae B1 to B12 and the lumbar vertebrae B13 to B17 on the 3D images 201 corresponding to the estimation data, and corrects a weight parameter to decrease an error $(X_{pi}-X_{3di}, Y_{pi}-Y_{3di}, Z_{pi}-Z_{3di})$ (i=1 to 17) between the estimation data and the correct answer data for the centroids C1 to C17 and an error $(X_{spi}-X_{3dspi}, Y_{spi}-Y_{3dspi}, Z_{spi}-Z_{3dspi})$ (i=1 to 17) between the estimation data and the correct answer data for the spinous processes SP1 to SP17 using the error back propagation method (BP).

The SCAE unit 12 corrects weights by repeating processing of the error back propagation method described above using the data set of the large number of 3D images and CT images stored in the learning image memory 22 and the X-ray image memory 21, thereby performing learning. As a result, the SCAE unit 12 may acquire an algorithm of the CNN for outputting the 3D coordinates $(X_{spi}, Y_{spi}, Z_{spi})$ (i=1 to 17) of the seventeen spinous processes SP1 to SP17 of the thoracic vertebrae B1 to B12 and the lumbar vertebrae B13 to B17 on the 3D images 201 in addition to the coordinates $(X_{pi}, Y_{pi}, Z_{pi})$ (i=1 to 17) of the seventeen centroids C1 to C17 of the thoracic vertebrae B1 to B12 and the lumbar vertebrae B13 to B17 on the 3D images 201 when an unknown 3D image is read from the learning image memory 22.

<Estimation Phase>

Next, in step S41 of an estimation phase of FIG. 21, the image sensor 3 captures 3D images representing a 3D shape of the back surface of the human body. The captured unknown 3D image is stored in the learning image memory 22 of the storage device 2. The image acquisition unit 11 reads and acquires the unknown 3D image from the learning image memory 22.

Figure 23:
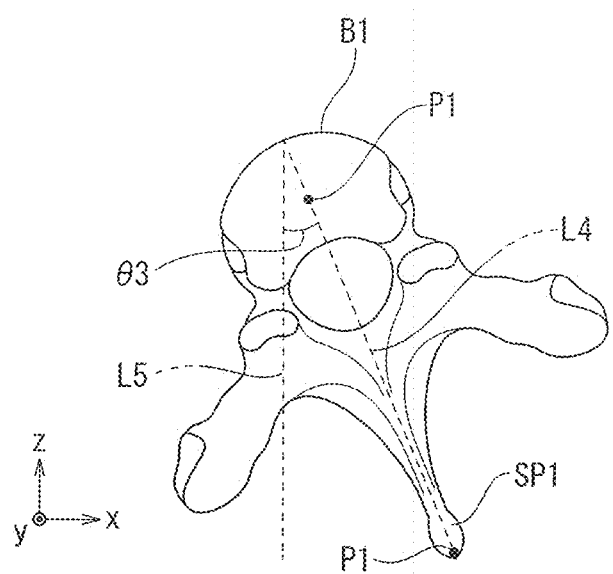
FIG. 23 is a schematic diagram illustrating an example of a method of calculating a rotation angle of the vertebral body according to the modification of the second embodiment of the present invention.

In step S42, the SCAE unit 12 of the CPU 1 estimates spinal-column arrangement including 3D coordinates of the seventeen centroids P1 to P17 of the thoracic vertebrae B1 to B12 and the lumbar vertebrae B13 to B17 from the unknown 3D image acquired by the image acquisition unit 11 and estimates 3D coordinates of each of seventeen spinous processes of the thoracic vertebrae B1 to B12 and the lumbar vertebrae B13 to B17 using learning data after machine learning stored in the learning data memory 23. For example, as illustrated in FIG. 23, the SCAE unit 12 estimates 3D coordinates of a position p1 of the spinous process SP1 of the thoracic vertebra B1. 3D coordinates of positions p2 to p17 of the other respective spinous processes SP2 to SP17 of the thoracic vertebrae B2 to B12 and the lumbar vertebrae B13 to B17 are similarly estimated. An estimation result of the spinal-column arrangement and the 3D coordinates of the spinous processes are stored in the estimation data memory 24.

In step S43, the angle calculation unit 13 of the CPU 1 reads the spinal-column arrangement estimated by the SCAE unit 12 from the estimation data memory 24 to calculate a Cobb angle θ2. The calculated Cobb angle θ2 is stored in the estimation data memory 24. Further, the angle calculation unit 13 of the CPU 1 calculates rotation angles of the thoracic vertebrae B1 to B12 and the lumbar vertebrae B13 to B17 from the spinal-column arrangement and the 3D coordinates of the spinous processes estimated by the SCAE unit 12. The rotation angles of the thoracic vertebrae B1 to B12 and the lumbar vertebrae B13 to B17 are calculated as angles at which midlines of the thoracic vertebrae B1 to B12 and the lumbar vertebrae B13 to B17 are inclined with respect to the front-back direction of the human body in a plane perpendicular to the vertical direction of the human body, and are indices for determining scoliosis.

For example, as illustrated in FIG. 23, a straight line L4 passing through the 3D coordinates of the centroid P1 of the thoracic vertebra B1 and the 3D coordinates of the position p1 of the spinous process SP1 is calculated as a midline. Then, an angle θ3 formed by the midline L4 and a straight line L5 parallel to the z-axis direction of the 3D images is calculated as a rotation angle. The angle calculation unit 13 similarly calculates the rotation angle θ3 for the other thoracic vertebrae B2 to B12 and lumbar vertebrae B13 to B17. The calculated rotation angle θ3 of each of the thoracic vertebrae B1 to B12 and the lumbar vertebrae B13 to B17 is stored in the estimation data memory 24.

In step S44, the image output control unit 14 of the CPU 1 reads the spinal-column arrangement estimated by the SCAE unit 12, the Cobb angle θ2 calculated by the angle calculation unit 13, and the rotation angle θ3 of each of the thoracic vertebrae B1 to B12 and the lumbar vertebrae B13 to B17 from the estimation data memory 24, and displays the read spinal-column arrangement, Cobb angle θ2, and rotation angle θ3 on, for example, a screen of the display corresponding to the output device 4.

As described above, according to the SCAE apparatus and the SCAE method according to the second embodiment, similarly to the first embodiment, it is possible to accurately estimate arrangement of spinal-column elements from 3D images using frameworks of AI with the CPU 1 using a machine learning scheme. Therefore, a doctor may accurately diagnose the presence or absence and a degree of scoliosis with reference to the estimated spinal-column arrangement and Cobb angle, and variation in diagnosis among doctors may be reduced.

Further, according to the SCAE apparatus and the SCAE method according to the modification of the second embodiment, it is possible to three-dimensionally estimate arrangement of the spinal-column elements from the 3D images using learning data obtained by the 3D images and the CT image as a data set. Further, it is possible to calculate the Cobb angle θ2 and the rotation angle θ3 of the spinal-column elements from the 3D arrangement of the spinal-column elements. Therefore, in addition to a current evaluation criterion of the magnitude of the Cobb angle of the X-ray images, information about 3D spinal-column arrangement, a 3D maximum Cobb angle, and a rotation angle of each vertebral body at the time of standing is further obtained. Thus, it is possible to predict progression of scoliosis, predict prognosis, and elucidate pathology, and there is a possibility that a new treatment method or treatment system may be established.

In the modification of the second embodiment, a case in which the Cobb angle θ2 and the rotation angle θ3 of the spinal-column elements are calculated from the 3D arrangement of the spinal-column elements has been illustrated. However, only the rotation angle θ3 of the spinal-column elements may be calculated. The rotation angle θ3 of the spinal-column elements may be utilized as a material for determination of scoliosis by the doctor by being calculated and output (displayed).

In addition, the angle calculation unit 13 of the CPU 1 may read the rotation angle θ3 of each of the thoracic vertebrae B1 to B12 and the lumbar vertebrae B13 to B17 from the estimation data memory 24 to determine the magnitude by comparing the rotation angle θ3 of each of the thoracic vertebrae B1 to B12 and the lumbar vertebrae B13 to B17 with a predetermined threshold value, extract a maximum value among the respective rotation angles θ3 of the thoracic vertebrae B1 to B12 and the lumbar vertebrae B13 to B17, or sort the respective rotation angles θ3 of the thoracic vertebrae B1 to B12 and the lumbar vertebrae B13 to B17 in stages using the predetermined threshold value. Further, a calculation result by the angle calculation unit 13 of the CPU 1 may be appropriately displayed on the screen of the display corresponding to the output device 4.

Other Embodiments

As described above, the present invention has been described by the first and second embodiments. However, it should not be understood that the description and drawings implementing a part of this disclosure limit the present invention. From this disclosure, various alternative embodiments, examples and operational techniques will be apparent to those skilled in the art.

For example, in the first and second embodiments of the present invention, a description has been given of the case of estimating arrangement of seventeen spinal-column elements corresponding to the thoracic vertebrae B1 to B12 and the lumbar vertebrae B13 to B17 including twelve thoracic vertebrae and five lumbar vertebrae. However, estimated arrangement of spinal-column elements is not limited to the seventeen spinal-column elements. For example, less than seventeen thoracic vertebrae and lumbar vertebrae may be targeted, and more than seventeen spinal-column elements including a cervical vertebra above the thoracic vertebrae and a sacral vertebra and a caudal vertebra below the lumbar vertebrae may be targeted.

In addition, the first embodiment illustrates a case in which spinal-column arrangement, etc. is two-dimensionally estimated from an unknown moire image using learning data obtained by a data set of the moire image corresponding to 2D data and a standing X-ray front image corresponding to 2D data as X-ray images. In addition, the second embodiment illustrates a case in which spinal-column element, etc. is three-dimensionally estimated from an unknown 3D image using learning data obtained by a data set of 3D images corresponding to 3D data and CT images corresponding to 3D data as X-ray images. Here, the first and second embodiments of the present invention may be combined to two-dimensionally or three-dimensionally estimate spinal-column arrangement, etc. from an unknown moire image using learning data obtained by a data set of the moire image and CT images as X-ray images. Alternatively, spinal-column arrangement, etc. may be two-dimensionally estimated from an unknown 3D image using learning data obtained by a data set of 3D images and a standing X-ray front image as X-ray images.

Further, the second embodiment illustrates the case of separately preparing 3D images captured by the 3D imaging machine and CT images as X-ray images. However, a 3D shape of the human body surface such as the back of the human body may be extracted as 3D images from CT images. Spinal-column arrangement, etc. may be three-dimensionally estimated from an unknown 3D image obtained by the 3D imaging machine using learning data obtained by this extracted 3D image and the CT image as a data set.

Furthermore, in the first and second embodiments of the present invention, a description has focused on the 3D shape of the back of the human body (back surface side of the human body). However, 3D images indicating a shape of a human body surface on the back surface side of the human body may correspond to a range image captured using a range image sensor from the back surface side of the human body. 3D images necessary for estimation of spinal-column arrangement, etc. is not necessarily limited to 3D images on the back surface side of the human body. In the case of 3D images including a position in which spinal-column arrangement is reflected, a surface image of the entire surface of the human body including the front surface side of the human body viewed from a 360° direction may be used as original data. In addition, data of a 3D shape on the back surface side of the human body may be selected from the inside of the original data of the obtained surface image viewed from the 360° direction.

Furthermore, since spinal-column arrangement is most reflected on the back surface side of the human body, it is suitable to use 3D images on the back surface side of the human body. However, when sufficient data is accumulated, it is possible to use 3D images on the front surface side of the human body. Further, it is possible to estimate 3D spinal-column arrangement, etc. using learning data obtained by the 3D images on the front surface side of the human body together with CT images, etc. as a data set. That is, since spinal-column arrangement, etc. may be estimated in the case of data of 3D images on the human body surface in which 3D spinal-column arrangement can be reflected, the 3D images is not limited only to the 3D images of the back of the human body.

In addition, when a wavelength of the 3D imaging machine using to capture 3D images as the image sensor 3 according to the second embodiment is set to a wavelength of an infrared ray or a submillimeter wave, it is possible to acquire 3D images of the human body surface through a thin cloth. Therefore, even in a clothed state, it is possible to accurately capture the 3D images of the human body surface, and to estimate spinal-column arrangement, etc. In addition, even in the case of a 3D imaging machine having a wavelength other than that of the infrared ray or the submillimeter wave, it is possible to capture the 3D images of the human body surface even in the clothed state by eliminating noise.

INDUSTRIAL APPLICABILITY

The present invention may be used for a SCAE apparatus, a SCAE method, and a SCAE program capable of estimating arrangement of spinal-column elements from 3D images or moire images, facilitating diagnosis of scoliosis by a doctor, confirmation of a spinal-column by a determiner, etc., and reducing medical exposure by unnecessary X-ray inspection.

EXPLANATIONS OF LETTERS OR NUMERALS

1 CENTRAL PROCESSING UNIT (CPU)
2 STORAGE DEVICE
3 IMAGE SENSOR
4 OUTPUT DEVICE
10 IMAGE PROCESSOR
11 IMAGE ACQUISITION UNIT
12 SPINAL-COLUMN ARRANGEMENT ESTIMATION-UNIT
13 ANGLE CALCULATION UNIT
14 IMAGE OUTPUT CONTROL UNIT
21 X-RAY IMAGE MEMORY
22 LEARNING IMAGE MEMORY
23 LEARNING DATA MEMORY
24 ESTIMATION DATA MEMORY
31 LIGHT PROJECTING UNIT
32 CAMERA
100 HUMAN BODY
101, 101a, 101b, 101c, 103 MOIRE IMAGE
102 X-RAY IMAGE (STANDING X-RAY FRONT IMAGE)
201, 203 3D IMAGE
202 X-RAY IMAGE (CT IMAGE)
B1 TO B12 SPINAL-COLUMN ELEMENT (THORACIC VERTEBRA)
B13 TO B17 SPINAL-COLUMN ELEMENT (LUMBAR VERTEBRA)
C1 TO C17, P1 TO P17 CENTROID
F1 TO F4 POINTS AT FOUR CORNERS OF THORACIC VERTEBRA
L1, L2, L3 CURVE
N1 TO N4 POINT OF BASE OF NECK
V1 TO V17 VERTICAL LINE
$\theta 1$, $\theta 2$ COBB ANGLE
$\theta 3$ ROTATION ANGLE

The invention claimed is:
1. A spinal-column arrangement estimation-apparatus comprising:
a learning processor configured to:
prepare one or more data sets of 3D surface image, representing a 3D shape of a back surface of a human body, and tomography image for each person;
extract anatomical feature points of spinal-column arrangement on each tomography image and store the extracted anatomical feature points as labeled data of each tomography image;
align the 3D surface image and the tomography image for each data set; and
train a hierarchical or deep neural network with learnable weight parameters based on the one or more data sets of the aligned 3D surface image and the tomography image with extracted anatomical feature points of spinal-column arrangement, and
an estimating processor configured to:
prepare an unknown 3D surface image with unknown coordinates of the spinal-column arrangement;
estimate coordinates of the spinal-column arrangement on the unknown 3D surface image based on the trained neural network; and
calculate at least one of a Cobb angle and a rotation angle of the spinal-column arrangement of the unknown 3D surface image based on the estimated coordinates of the spinal-column arrangement.
2. The spinal-column arrangement estimation-apparatus of claim 1, wherein the estimating processor estimates coordinates of centroids of a plurality of spinal-column elements included in a spinal-column of the human body from which the tomography image is acquired as the spinal-column arrangement.
3. The spinal-column arrangement estimation-apparatus of claim 2, wherein the estimating processor calculates a curve connecting the coordinates of the centroids of the plurality of spinal-column elements.
4. The spinal-column arrangement estimation-apparatus of claim 2, wherein the estimating processor estimates coordinates of spinous processes of the plurality of spinal-column elements, and estimates the rotation angle based on the coordinates of the centroids of the plurality of spinal-column elements and the coordinates of spinous processes.
5. The spinal-column arrangement estimation-apparatus of claim 1, wherein the 3D surface image acquired by the learning processor is a 3D image captured by a 3D imaging machine.
6. The spinal-column arrangement estimation-apparatus of claim 1, wherein the 3D surface image acquired by the learning processor is a moire image including a moire fringe of the back surface of the human body captured by a moire imaging machine.
7. A spinal-column arrangement estimation method comprising:
preparing one or more data sets of 3D surface image, representing a 3D shape of a back surface of a human body, and tomography image for each person;

extracting anatomical feature points of spinal-column arrangement on each tomography image and store the extracted anatomical feature points as labeled data of each tomography image;

aligning the 3D surface image and the tomography image for each data set; and training a hierarchical or deep neural network with learnable weight parameters based on the one or more data sets of the aligned 3D surface image and the tomography image with extracted anatomical feature points of spinal-column arrangement;

preparing an unknown 3D surface image with unknown coordinates of the spinal-column arrangement;

estimating coordinates of the spinal-column arrangement on the unknown 3D surface image based on the trained neural network; and calculating at least one of a Cobb angle and a rotation angle of the spinal-column arrangement of the unknown 3D surface image based on the estimated coordinates of the spinal-column arrangement.

8. A non-transitory computer-readable recording medium storing a program for spinal-column arrangement estimation, wherein the program includes software instructions which, when executed by a computer, comprise:

preparing one or more data sets of 3D surface image, representing a 3D shape of a back surface of a human body, and tomography image for each person;

extracting anatomical feature points of spinal-column arrangement on each tomography image and store the extracted anatomical feature points as labeled data of each tomography image;

aligning the 3D surface image and the tomography image for each data set; and training a hierarchical or deep neural network with learnable weight parameters based on the one or more data sets of the aligned 3D surface image and the tomography image with extracted anatomical feature points of spinal-column arrangement;

preparing an unknown 3D surface image with unknown coordinates of the spinal-column arrangement;

estimating coordinates of the spinal-column arrangement on the unknown 3D surface image based on the trained neural network; and calculating at least one of a Cobb angle and a rotation angle of the spinal-column arrangement of the unknown 3D surface image based on the estimated coordinates of the spinal-column arrangement.

* * * * *